(12) United States Patent
Richards et al.

(10) Patent No.: US 7,439,397 B2
(45) Date of Patent: *Oct. 21, 2008

(54) PHENOL DERIVATIVE

(75) Inventors: Ivan Richards, Kalamazoo, MI (US); Sue K. Cammarata, Portage, MI (US); Craig D. Wegner, Mundelein, IL (US); Michael Hawley, Kalamazoo, MI (US); Mark Peter Warchol, Kalamazoo, MI (US); Mark Kontny, Libertyville, IL (US); Walter Morozowich, Kalamazoo, MI (US); Karen Patrice Kolbasa, Schoolcraft, MI (US); Malcolm Wilson Moon, Kalamazoo, MI (US); Dominique Bonafoux, St. Louis, MO (US); Sergey Gregory Wolfson, Chesterfield, MO (US); Patrick James Lennon, Webster Groves, MO (US)

(73) Assignee: Pfizer Inc, New York, NY (US)

( * ) Notice: Subject to any disclaimer, the term of this patent is extended or adjusted under 35 U.S.C. 154(b) by 467 days.

This patent is subject to a terminal disclaimer.

(21) Appl. No.: 11/074,914

(22) Filed: Mar. 8, 2005

(65) Prior Publication Data

US 2005/0148672 A1 Jul. 7, 2005

(51) Int. Cl.
  *C07C 211/08* (2006.01)
  *A61K 31/205* (2006.01)
  *A01N 33/12* (2006.01)
(52) U.S. Cl. .................. 564/285; 564/554; 564/643
(58) Field of Classification Search ............. 514/643, 514/554; 564/285
See application file for complete search history.

(56) References Cited

U.S. PATENT DOCUMENTS

| 2,592,191 | A | 4/1952 | Ruddy |
| 3,480,623 | A | 11/1969 | Consonni et al. |
| 3,505,337 | A | 4/1970 | Zeile et al. |
| 5,036,098 | A | 7/1991 | Kimura et al. |
| 5,096,890 | A | 3/1992 | Cross et al. |
| 5,382,600 | A | 1/1995 | Jonsson et al. |
| 5,559,269 | A | 9/1996 | Johansson et al. |
| 5,922,914 | A | 7/1999 | Gage et al. |
| 6,313,132 | B1 * | 11/2001 | Johansson et al. ........... 514/277 |
| 6,538,035 | B2 | 3/2003 | Gillberg et al. |
| 6,890,920 | B2 * | 5/2005 | Richards et al. ........ 514/212.01 |
| 7,119,121 | B2 * | 10/2006 | Slatter et al. ................. 514/648 |
| 7,291,648 | B2 * | 11/2007 | Slatter et al. ................. 514/648 |
| 2004/0242569 | A1 * | 12/2004 | Lennon et al. ........... 514/223.8 |

FOREIGN PATENT DOCUMENTS

| CA | 2066248 | 8/1998 |
| DE | 0106643 | 6/1974 |
| EP | 0418716 | 3/1991 |
| GB | 0940540 | 10/1963 |
| WO | WO9510269 | 4/1995 |
| WO | WO9510270 | 4/1995 |
| WO | WO9829402 | 7/1998 |
| WO | WO9843942 | 10/1998 |
| WO | WO0235245 | 5/2002 |

OTHER PUBLICATIONS

Eglen et al, *Trends in Pharmacological Sciences*, 22(8):409-414 (2001).
Gould, *International Journal of Pharmaceutics*, 33(1-3):201-217 (1986)—Abstract only.
Stewart et al, *The Journal of Urology*, 115:558-559 (1976).
Ruffmann, *Journal of International Medical Research*, 16:317-330 (1988).
Yono et al, *European Journal of Pharmacology*, 368:223-230 (1999).
Postlind et al, *Drug and Metabolism Disposition*, 26(4):289-293 (1998).
Nilvebrant et al, *Pharmacology & Toxicology*, 81:169-172 (1997).
Weber, *Annals of Allergy*, 65:348-350 (1990).

* cited by examiner

*Primary Examiner*—Rita J Desai
*Assistant Examiner*—John Mabry
(74) *Attorney, Agent, or Firm*—Gregg C. Benson; Robert T. Ronau

(57) ABSTRACT

The compound 2-[(1R)-3-(diisopropylamino)-1-phenylpropyl]-4-(trifluoromethyl) phenol may be used to prepare the compound (3R)-3-[2-hydroxy-5-(trifluoromethyl)phenyl]-N,N-diisopropyl-N-methyl-3-phenylpropan-1-aminium bromide by reaction with methyl bromide.

2 Claims, 7 Drawing Sheets

PHENOL DERIVATIVE

This application claims the benefit of U.S. application Ser. No. 10/280,906 filed Oct. 25, 2002, now U.S. Pat. No. 6,890,920 U.S. Provisional Patent Application No. 60/348,930, filed Oct. 26, 2001, U.S. Provisional Patent Application No. 60/361,979, filed Mar. 6, 2002, and U.S. Provisional Patent Application No. 60/391,521, filed Jun. 25, 2002, and the entire disclosures of which are herein incorporated by reference.

TECHNICAL FIELD

The present invention concerns a novel class of quaternary ammonium compounds, pharmaceutical compositions containing the same, the compounds for use as medicaments, and use of the compounds for the manufacture of specific medicaments. The present invention also concerns a method of treatment involving administration of the compounds.

The novel compounds are useful as antimuscarinic agents. In particular, the novel compounds are useful for the treatment of asthma, a group of breathing disorders termed Chronic Obstructive Pulmonary Disease (COPD), allergic rhinitis, and rhinorrhea due to the common cold.

BACKGROUND OF THE INVENTION

U.S. Pat. No. 5,382,600 discloses (substituted) 3,3-diphenylpropylamines useful for treating urinary incontinence. In particular, it discloses 2-[(1R)-3-(diisopropylamino)-1-phenylpropyl]-4-methylphenol, also known as N,N-diisopropyl-3-(2-hydroxy-5-methylphenyl)-3-phenylpropylamine, with the generic name of tolterodine, as being useful to treat urinary incontinence. Tolterodine is the compound of Example 22 of U.S. Pat. No. 5,382,600.

It is preferred that tolterodine is prepared by the processes of International Publication WO98/29402 (U.S. Pat. No. 5,922,914).

H Postlind et al, Drug Metabolism and Disposition, 26(4): 289-293 (1998) discloses that tolterodine is a muscarinic receptor antagonist. It is presently being sold in a number of different countries for treatment of urinary incontinence under the name Detrol®, marketed by Pharmacia. When tolterodine is used to treat urinary incontinence it is administered perorally as a tablet. The major, active metabolite of tolterodine is the 5-hydroxymethyl derivative of tolterodine. U.S. Pat. No. 5,559,269 and H Postlind et al, Drug Metabolism and Disposition, 26(4): 289-293 (1998) disclose hydroxytolterodine. U.S. Pat. No. 5,559,269 discloses this compound as being useful to treat urinary incontinence. Pharmacol. Toxicol., 81: 169-172 (1997) discloses that hydroxytolterodine has antimuscarinic activity.

The international patent application WO98/43942 discloses therapeutically active diarylpropylamines, which have favorable anticholinergic properties, and which can be used for the treatment of disorders related to urinary incontinence.

WO 02/34245 discloses the use of tolterodine for treating asthma, COPD, and allergic rhinitis.

The currently marketed administration form of tolterodine is film-coated tablets containing 1 mg or 2 mg of tolterodine L-tartrate, or extended release capsules containing 2 mg or 4 mg of tolterodine L-tartrate for release in the gastrointestinal tract. Consumers constantly require alternative delivery forms with favorable efficacy and/or which simplify the treatment, thus improving their quality of life.

Atropine methonitrate and ipratropium are quaternary ammonium derivatives of atropine. Ipratropium bromide is used by inhalation to produce bronchodilation. Ipratropium is 8-isopropylnoratropine methobromide and is disclosed in U.S. Pat. No. 3,505,337.

Yono M et al, European Journal of Pharmacology (1999) 368:223-230, is concerned with the pharmacological effects of tolterodine, an antimuscarinic drug, in isolated human urinary bladder smooth muscle.

Ruffmann R et al, The Journal of International Medical Research (1998) 16:317-330, reviews use of flavoxate hydrochloride or alternative compounds, such as terodiline hydrochloride and emepronium bromide, in the treatment of urge incontinence.

Stewart B H et al, The Journal of Urology (1976) 115:558-559 discloses therapy of mild to moderate stress urinary incontinence with a combination of phenylpropanolamine hydrochloride, chlorpheniramine maleate, and isopropamide iodide in a sustained release capsule.

WO 95/10269 and WO 95/10270 disclose the use of R- and S-terodiline, respectively, as drugs for treating conditions related to the compounds' activities as anticholinergic agents.

Despite the above advances in the art, it is desirable to develop novel pharmaceutical compounds that further improve the quality of life for a large number of individuals.

SUMMARY OF THE INVENTION

For these and other purposes, it is an object of the present invention to provide highly efficient pharmaceutical compounds for treatment of asthma.

It is also an object of the present invention to provide highly efficient pharmaceutical compounds for treatment of Chronic Obstructive Pulmonary Disease (COPD).

It is a further object of the present invention to provide highly efficient pharmaceutical compounds for treatment of allergic rhinitis.

It is an object of the present invention to provide highly efficient pharmaceutical compounds for treatment of rhinorrhea due to the common cold.

It is also an object of the present invention to provide pharmaceutically effective 3,3-diphenylpropylamine derivatives having an increased residence time in lung upon pulmonary administration.

It is an object of the present invention to provide a novel class of 3,3-diphenylpropylamine derivatives having favorable properties.

For these and other objects that will be evident from the following disclosure, the present invention provides a quaternary ammonium compound of the formula

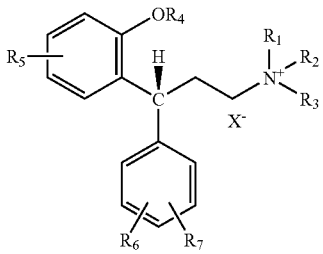

and any stereoisomers thereof, wherein $R_1$, $R_2$ and $R_3$ independently represent $C_1$-$C_6$ alkyl, optionally substituted with phenyl or hydroxyl, or both, and wherein any two of $R_1$, $R_2$ and $R_3$ may form a ring together with the quaternary ammonium nitrogen;

$R_4$ represents
—H,
—$CH_3$, or
—CO—$R_{4-1}$ wherein $R_{4-1}$ represents
—($C_1$-$C_4$ alkyl),
—($C_1$-$C_4$ alkoxy), or
—$NR_{4-2}R_{4-3}$, wherein $R_{4-2}$ and $R_{4-3}$ independently represent —H or —($C_1$-$C_4$ alkyl), and $R_5$, $R_6$ and $R_7$ independently represent
—H,
—$OCH_3$,
—OH,
—$CONH_2$,
—$SO_2NH_2$,
—F, —Cl, —Br, —I,
—$CF_3$, or
—($C_1$-$C_4$ alkyl), optionally substituted with one or two
—OH,
—($C_1$-$C_4$ alkoxy),
—COOH, or
—CO—O—($C_1$-$C_3$ alkyl), and $X^-$ represents an anion of a pharmaceutically acceptable acid.

In an embodiment of the compound according to the invention, the carbon stereocenter is (R). In another embodiment of the compound according to the invention, the carbon stereocenter is (S). In yet another embodiment, the compound according to the invention is a mixture of stereoisomers.

In a preferred embodiment of the compound according to the invention, at least one of $R_1$, $R_2$ and $R_3$ represents $C_1$-$C_3$ alkyl. In a more preferred embodiment, at least one, preferably at least two, of $R_1$, $R_2$ and $R_3$ represents isopropyl. In another more preferred embodiment, at least one of $R_1$, $R_2$ and $R_3$ represents methyl. In yet another more preferred embodiment, at least one of $R_1$, $R_2$ and $R_3$ represents ethyl.

In one preferred embodiment of the compound according to the invention, $R_1$ and $R_2$ jointly form a ring together with the quaternary ammonium nitrogen. In a more preferred embodiment, said ring comprises from 4 to 6 carbon atoms.

In a preferred embodiment of the compound according to the invention, $R_4$ represents —H, —$CH_3$, or —CO—$R_{4-1}$, wherein $R_{4-1}$ represents $C_1$-$C_4$ alkyl. In a more preferred embodiment, $R_4$ represents —H.

In a preferred embodiment of the compound according to the invention, $R_5$ represents —H, —Br, —Cl, —$CH_3$, or —$CH_2OH$, more preferably —$CH_3$.

In a preferred embodiment of the compound according to the invention, at least one, more preferably both, of $R_6$ and $R_7$ represents —H.

In a preferred embodiment of the compound according to the invention, $X^-$ is selected from the group consisting of the anions of the following acids: tartaric, hydrochloric, hydrobromic, hydroiodic, sulfuric, phosphoric, nitric, citric, methanesulfonic, $CH_3$—$(CH_2)_n$—COOH where n is 0 thru 4, HOOC—$(CH_2)$n—COOH where n is 1 thru 4, HOOC—CH=CH—COOH, and benzoic. In a more preferred embodiment, $X^-$ is selected from the group consisting of iodide, bromide, and chloride. In an even more preferred embodiment, $X^-$ represents iodide. In another even more preferred embodiment, $X^-$ represents chloride. In yet another even more preferred embodiment, $X^-$ represents bromide.

More specifically, preferred embodiments of the compound according to the invention include the title compounds of the examples. Particularly preferred embodiments are selected from the group consisting of (3R)-3-(2-hydroxy-5-methylphenyl)-N,N-diisopropyl-N-methyl-3-phenylpropan-1-aminium iodide, (3R)-3-(2-hydroxy-5-methylphenyl)-N,N-diisopropyl-N-methyl-3-phenylpropan-1-aminium bromide, and (3R)-3-(2-hydroxy-5-methylphenyl)-N,N-diisopropyl-N-methyl-3-phenylpropan-1-aminium chloride.

Moreover, the present invention provides a pharmaceutical composition comprising a therapeutically effective amount of a quaternary ammonium compound according to the invention, and a suitable pharmaceutical carrier therefor.

The present invention also provides a quaternary ammonium compound according to the invention for use as a medicament.

The present invention provides use of a quaternary ammonium compound according to the invention for the manufacture of a medicament for treating asthma, chronic obstructive pulmonary disease (COPD), allergic rhinitis, rhinorrhea due to the common cold, or urinary disorder.

Finally, the present invention provides a method of treating asthma, chronic obstructive pulmonary disease (COPD), allergic rhinitis, rhinorrhea due to the common cold, or urinary disorder in a mammal, including man, comprising administering to said mammal, in need of such a treatment, a therapeutically effective amount of a quaternary ammonium compound according to the invention.

BRIEF DESCRIPTION OF THE DRAWINGS

FIGS. 1-3 are diagrams showing average enhanced pause (lung resistance) as a function of time upon inhalation of quaternary ammonium salts according to the invention in Balb/c mice.

DESCRIPTION OF THE INVENTION

Figure 1:
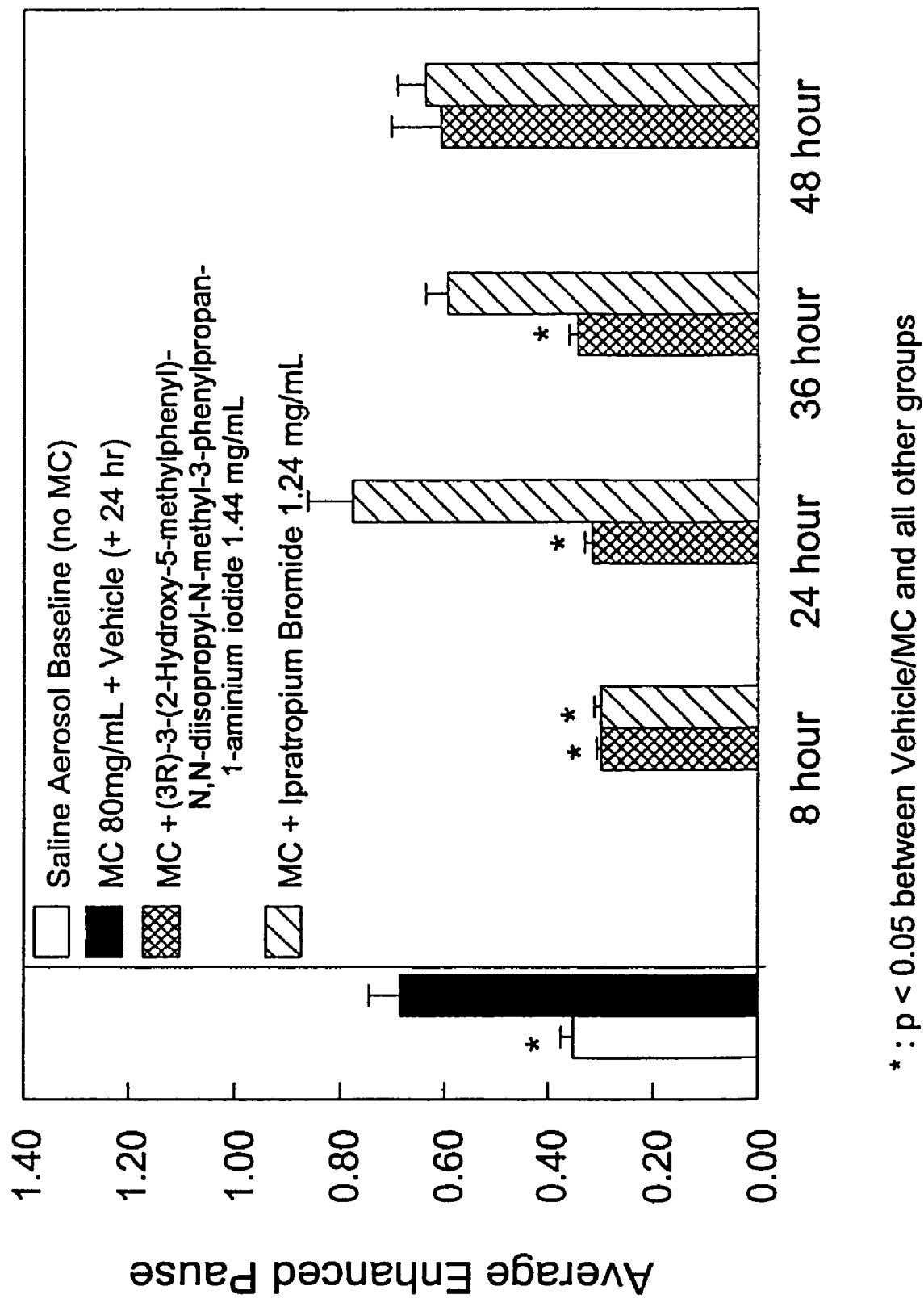

In describing the preferred embodiment, certain terminology will be utilized for the sake of clarity. Such terminology is intended to encompass the recited embodiments, as well as all technical equivalents that operate in a similar manner for a similar purpose to achieve a similar result. To the extent that any pharmaceutically active compound is disclosed or claimed, it is expressly intended to include all active metabolites produced in vivo, and, is expressly intended to include all enantiomers, isomers or tautomers where the compound is capable of being present in its enantiomeric, isomeric or tautomeric form.

The compounds of the invention can be prepared by one skilled in the art just by knowing the chemical structure of the compound to be prepared. The invention is the compounds themselves, not the process chemistry to make them. The chemistry is known to those skilled in the art.

Accordingly, the compounds of the present invention are quaternary ammonium compounds and are prepared by means, well known to those skilled in the art, for preparing quaternary ammonium compounds from tertiary amines, using the tertiary amines of U.S. Pat. No. 5,382,600 and other known compounds as starting materials. The general term "quaternary ammonium compound" relates to any compound that can be regarded as derived from ammonium hydroxide or an ammonium salt by replacement of all four hydrogen atoms of the $NH_4^+$-ion by organic groups.

The specific compounds are for nomenclature reasons (see e.g. Chemical Abstracts) named as "aminium" compounds, but it is possible to use the term "ammonium" in the names. For example, (3R)-3-(2-hydroxy-5-methylphenyl)-N,N-diisopropyl-N-methyl-3-phenylpropan-1-aminium bromide can also be named as an ammonium compound: (3R)-[3-(2-hydroxy-5-methylphenyl)-3-phenylpropyl]diisopropylmethylammonium bromide.

More specifically, the invention concerns quaternary ammonium compounds of the formula:

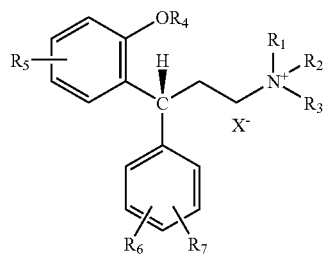

and any stereoisomers thereof, wherein $R_1$-$R_7$ and $X^-$ are as follows.

$R_1$, $R_2$ and $R_3$ independently represent $C_1$-$C_6$ alkyl, optionally substituted with phenyl or hydroxyl, or both, and any two of $R_1$, $R_2$ and $R_3$ may form a ring together with the quaternary ammonium nitrogen.

$R_4$ represents —H, —$CH_3$, or —CO—$R_{4-1}$, wherein $R_{4-1}$ represents —($C_1$-$C_4$ alkyl), —($C_1$-$C_4$ alkoxy), or —$NR_{4-2}$$R_{4-3}$, wherein $R_{4-2}$ and $R_{4-3}$ independently represent —H or —($C_1$-$C_4$ alkyl).

$R_5$, $R_6$ and $R_7$ independently represent —H, —$OCH_3$, —OH, —$CONH_2$ (carbamoyl), —$SO_2NH_2$ (sulphamoyl), —F, —Cl, —Br, —I, —$CF_3$, or —($C_1$-$C_4$ alkyl), optionally substituted with one or two —OH, —($C_1$-$C_4$ alkoxy), —COOH, or —CO—O—($C_1$-$C_3$ alkyl), and $X^-$ represents an anion of a pharmaceutically acceptable acid.

By way of example, a tertiary amine according to U.S. Pat. No. 5,382,600, or its salt, is dissolved in a suitable solvent. The tertiary amine is allowed to react with an organic substrate, e.g. an organic halide.

The substrate contains a $C_1$-$C_6$ alkyl, preferably a $C_1$-$C_3$ alkyl, optionally substituted with phenyl, and a leaving group. The identity of the leaving group is not critical, but it is preferred that the leaving group is a halide, such as iodide or bromide. Thus, exemplary substrates include methyl iodide, methyl bromide, ethyl iodide, propyl iodide, benzyl bromide or benzyl iodide.

The resulting reaction product is a quaternary ammonium compound, which is readily crystallized in suitable solvents, known to those skilled in the art. The crystals thus produced are quaternary ammonium salts. Their identity is confirmed by standard methods, such as melting point determination, nuclear magnetic resonance (NMR) analysis and mass spectrometry.

The quaternary ammonium compounds of the invention have at least one stereocenter, i.e. the carbon in position 3 ($C_3$ in the formula below), to which two (substituted) aryl groups are attached optionally, there may be a second stereocenter (when $R_1$, $R_2$ and $R_3$ all are different), the positively charged quaternary ammonium nitrogen atom. See the general formula:

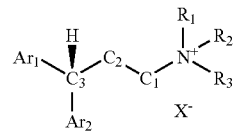

wherein $Ar_1$ and $Ar_2$ denote (substituted) aryl groups, $R_1$, $R_2$, $R_3$ and $X^-$ are as above, and $C_1$, $C_2$ and $C_3$ denote individual carbon atoms in the propylammonium backbone. Accordingly, stereoisomers (enantiomers and/or diastereomers) are produced. All stereoisomers have useful activity. Therefore, the invention includes use of each stereoisomer separately, as well as mixtures thereof. Specifically, the stereoisomers in which the $C_3$ carbon stereocenter is in the (R) form have useful activity. Moreover, the stereoisomers in which the $C_3$ carbon stereocenter is in the (S) form have useful activity. A mixture of stereoisomers, comprising the stereoisomers in which the $C_3$ carbon stereocenter is in the (R) form and the stereoisomers in which the $C_3$ carbon stereocenter is in the (S) form, also has useful activity.

The quaternary ammonium compounds of the invention are preferably administered as salts with a pharmaceutically acceptable acid. Where $R_4$ is —H, the compounds can be isolated as internal salts, which have a phenoxide anion to balance the positive charge on the quaternized nitrogen. The preferred pharmaceutically acceptable salts include salts of the following acids: tartaric, hydrochloric, hydrobromic, hydroiodic, sulfuric, phosphoric, nitric, citric, methanesulfonic, $CH_3$—$(CH_2)_n$—COOH where n is 0 thru 4, HOOC—$(CH_2)_n$—COOH where n is 1 thru 4, HOOC—CH=CH—COOH, and benzoic. For other acceptable salts, see Int. J. Pharm., 33, 201-217 (1986). Particularly preferred salts are chloride, iodide and bromide salts, especially bromide salts and iodide salts.

Accordingly, $X^-$ represents an anion of a pharmaceutically acceptable acid. Preferably, $X^-$ is selected from the following anions: tartrate, chloride, bromide, iodide, sulfate, phosphate(s), nitrate, citrate, methanesulfonate, carboxylates with from two to six carbon atoms, dicarboxylates with from two to six carbon atoms, maleate, fumarate, and benzoate. It is preferred that $X^-$ represents chloride, iodide or bromide, more preferred iodide or bromide.

The substituents $R_1$, $R_2$, $R_3$ may be the same or different. They are selected from the group comprising $C_1$-$C_6$ alkyls, preferably $C_1$-$C_5$ alkyls, straight or branched, optionally substituted with phenyl or hydroxyl, or both. Thus, $R_1$, $R_2$, $R_3$ independently represent methyl, ethyl, propyl, isopropyl, butyl, isobutyl, pentyl, isopentyl, hexyl, or isohexyl, optionally substituted with phenyl or hydroxyl, or both.

It is preferred that at least one of the substituents $R_1$, $R_2$, $R_3$ represents a $C_1$-$C_3$ alkyl, straight or branched, i.e. methyl, ethyl, propyl, or isopropyl. It is particularly preferred that one of the substituents $R_1$, $R_2$, $R_3$ represents methyl or ethyl, preferably methyl. It is also preferred that at least one, more preferred two, of the substituents $R_1$, $R_2$, $R_3$ represent(s) isopropyl. It is especially preferred that $R_1$ and $R_2$ each represent isopropyl, and $R_3$ represents methyl or ethyl, preferably methyl. The substituents $R_1$, $R_2$, and $R_3$ together contain at least 3 carbon atoms. It is preferred that the substituents $R_1$, $R_2$, and $R_3$ together contain at least 4 carbon atoms, more preferred at least 5 carbon atoms, even more preferred at least 6 carbon atoms.

According to another aspect of the invention, any two of $R_1$, $R_2$, and $R_3$ may jointly form a ring structure together with the positively charged nitrogen. It is preferred that the resulting ring structure comprises from four to six carbon atoms.

The substituent $R_4$ is attached via an oxygen atom to its aryl ring. The —$OR_4$ group is attached to the carbon atom in position 2 in the ring, with respect to the propylammonium group. The substituent $R_4$ may represent hydrogen, methyl or acyl (—CO—$R_{4-1}$), wherein acyl includes any one of the following: alkylcarbonyl, straight or branched, having from two to five carbon atoms, alkoxycarbonyl, straight or branched, having from two to five carbon atoms, and amide, optionally mono- or independently disubstituted with alkyl, straight or branched, having from one to four carbon atom(s). Accordingly, the substituent $R_{4-1}$ represents any one of the following: $C_1$-$C_4$ alkyl, straight or branched, $C_1$-$C_4$ alkoxy, straight or branched, and —$NR_{4-2}R_{4-3}$, wherein $R_{4-2}$ and $R_{4-3}$ may be the same or different and represent —H or —($C_1$-$C_4$ alkyl), straight or branched. Thus, the substituent $R_4$ may represent any one of the following: hydrogen, methyl or acyl, wherein the acyl group may be acetyl (ethanoyl), propanoyl, butanoyl, isobutanoyl, pentanoyl, isopentanoyl, methoxycarbonyl, ethoxycarbonyl, propoxycarbonyl, isopropoxycarbonyl, butoxycarbonyl, isobutoxycarbonyl, carbamoyl, N-methylcarbamoyl, N-ethylcarbamoyl, N-propylcarbamoyl, N-butylcarbamoyl, or an N,N-dialkylcarbamoyl, wherein the alkyl groups, straight or branched, are the same or different and have from 1 to 4 carbon atoms each. Examples of N,N-dialkylcarbamoyls in this position include N,N-dimethylcarbamoyl, N,N-diethylcarbamoyl, N,N-dipropylcarbamoyl, as well as N,N-diisobutylcarbamoyl, and N-propyl-N-butylcarbamoyl. It is preferred that $R_4$ represents hydrogen, since such compounds can be isolated as internal salts, which have a phenoxide anion to balance the positive charge on the quaternized nitrogen. It is also preferred that $R_4$ represents alkylcarbonyl, straight or branched, having from two to five carbon atoms, e.g. acetyl (ethanoyl), propanoyl, butanoyl, isobutanoyl, pentanoyl, or isopentanoyl. Moreover, it is preferred that $R_4$ represents methyl.

The substituent $R_5$ may be connected to any, otherwise not substituted, carbon atom in its aryl ring. In other words, $R_5$ is not connected to any of the carbon atoms to which the —$OR_4$ group or the (substituted) phenylpropanammonium group is connected, but $R_5$ may be connected to any one of the remaining four carbon atoms in its aryl ring.

$R_5$ may represent any one of the following: hydrogen, methoxy, hydroxyl, carbamoyl, sulphamoyl, halogen (fluorine, chlorine, bromine, iodine), trifluoromethyl or an alkyl group, straight or branched, having from one to four carbon atoms. Optionally, this alkyl group may be mono- or independently disubstituted with hydroxyl, with an alkoxy group, straight or branched, having from one to four carbon atoms, with carboxyl, or with alkoxycarbonyl (—CO—O—($C_1$-$C_3$ alkyl)), straight or branched, having from one to four carbon atoms. It is preferred that $R_5$ represents any one of the following: hydrogen, bromine, chlorine, methyl or hydroxymethyl. It is particularly preferred that $R_5$ represents methyl. If $R_5$ does not represent hydrogen, it is preferred that $R_5$ is situated opposite the —$OR_4$ group, i.e. at the carbon atom in position 5 in the ring, with respect to the propylammonium group.

The substituents $R_6$ and $R_7$ are connected to the same aryl ring, which is different from the aryl ring to which the substituents $R_4$ and $R_5$ are connected. $R_6$ and $R_7$ may be the same or different. $R_6$ and $R_7$ may independently represent any one of the following: hydrogen, methoxy, hydroxyl, carbamoyl, sulphamoyl, halogen (fluorine, chlorine, bromine, iodine), trifluoromethyl or an alkyl group, straight or branched, having from one to four carbon atoms. Optionally, this alkyl group may be mono- or independently disubstituted with hydroxyl, with an alkoxy group, straight or branched, having from one to four carbon atoms, with carboxyl, or with alkoxycarbonyl (—CO—O—($C_1$-$C_3$ alkyl)), straight or branched, having from one to four carbon atoms.

It is preferred that at least one, preferably both, of $R_6$ and $R_7$ represents hydrogen. When one, but not both, of $R_6$ and $R_7$ represents hydrogen, it is preferred that the other ($R_7$ or $R_6$, respectively) is attached to the carbon atom in position 2 in the ring, with respect to the propylammonium group. When neither $R_6$ nor $R_7$ represent hydrogen, it is preferred that one is attached to the carbon atom in position 2 and the other to any one of the carbon atoms in positions 3, 4, or 5, respectively, in the ring, with respect to the propylammonium group.

The novel class of compounds according to the present invention are antimuscarinic agents. "Antimuscarinic agents" refer to muscarinic receptor antagonists. Examples of known antimuscarinic agents include tolterodine, hydroxytolterodine, 2-(diisopropylamino)ethyl-1-phenylcyclopentanecarboxylate, propiverine, oxybutynin, trospium, darifenacin, temiverine, ipratropium, and tiotropium.

Propiverine is 1-methyl-4-piperidyl .alpha.,.alpha. -diphenyl-.alpha.-(n-propoxy)acetate and is disclosed in East German Pat. No. 106,643 and in CAS 82-155841s (1975). Oxybutynin is 4-(diethylamino)-2-butynylalphaphenylcyclohexaneglycolate and is disclosed in UK Pat. No. 940,540. Trospium is 3alpha-hydroxyspiro[1alphaH, 5alphaH-nortropane-8,1'pyrrolidinium] chloride benzilate and is disclosed in U.S. Pat. No. 3,480,623. Darifenacin is 3-Pyrrolidineacetamide, 1-[2-(2,3-dihydro-5-benzofuranyl)ethyl]-alpha,alpha-diphenyl-, and is disclosed in U.S. Pat. No. 5,096,890. Temiverine is benzeneacetic acid, .alpha.-cyclohexyl-.alpha.-hydroxy-, 4-(diethylamino)-1,1-dimethyl-2-butynyl ester and is disclosed in U.S. Pat. No. 5,036,098. Ipratropium is 8-isopropylnoratropine methobromide and is disclosed in U.S. Pat. No. 3,505,337. Tiotropium is (1-alpha,2-beta,4-beta,5-alpha, 7-beta)-7-[(hydroxydi-(2-thienyl)acetyl)oxy]-9,9-dimethyl-3-oxa-9-azoniatricyclo [3.3.1.02,4]nonane and is disclosed in EP 418,716.

The compounds of the invention have anti-cholinergic properties. Thus, they are useful for the treatment of acetylcholine-mediated disorders. In particular, they are useful for treating asthma, chronic obstructive pulmonary disease (COPD), allergic rhinitis, and rhinorrhea due to the common cold.

"Asthma" refers to a chronic lung disease causing bronchoconstriction (narrowing of the airways) due to inflammation (swelling) and tightening of the muscles around the airways. The inflammation also causes an increase in mucus production, which causes coughing that may continue for extended periods. Asthma is characterized by recurrent episodes of breathlessness, wheezing, coughing, and chest tightness, termed exacerbations. The severity of exacerbations can range from mild to life threatening. The exacerbations can be a result of exposure to e.g. respiratory infections, dust, mold, pollen, cold air, exercise, stress, tobacco smoke, and air pollutants.

"COPD" refers to Chronic Obstructive Pulmonary Disease, primarily associated with past and present cigarette smoking. It involves airflow obstruction, mainly associated with emphysema and chronic bronchitis. Emphysema causes irreversible lung damage by weakening and breaking the air sacs within the lungs. Chronic Bronchitis is an inflammatory disease, which increases mucus in the airways and bacterial infections in the bronchial tubes, resulting in obstructed airflow.

"Allergic rhinitis" refers to acute rhinitis or nasal rhinitis, including hay fever. It is caused by allergens such as pollen or dust. It may produce sneezing, congestion, runny nose, and itchiness in the nose, throat, eyes, and ears.

"Rhinorrhea due to the common cold" refers to watery discharge from the nose in association with a virus infection, such as the common cold. The rhinorrhea may be caused by rhinitis due to a virus infection (such as the common cold).

"Urinary disorders" and symptoms thereof include some or all of the following: urgency, frequency, incontinence, urine leakage, enuresis, dysuria, hesitancy, and difficulty of emptying bladder. In particular, urinary disorders include urinary incontinence, caused by e.g. unstable or overactive urinary bladder.

Overactive urinary bladder encompasses variants of urinary disorders, including overactive detrusor (detrusor instability, detrusor hyperreflexia) and sensory urgency, as well as symptoms of detrusor overactivity, e.g. urge incontinence, urgency, urinary frequency, and LUTS (Lower Urinary Tract Symptoms), including obstructive urinary symptoms, such as slow urination, dribbling at the end of urination, inability to urinate and/or the need to strain to urinate at an acceptable rate, or irritating symptoms such as frequency, dry overactive bladder, and/or urgency).

Other conditions are also included, which give rise to urinary frequency, urgency and/or urge incontinence. Overactive bladder disorders also include nocturia and mixed incontinence. While overactive bladder is often associated with detrusor muscle instability, disorders of bladder function may also be due to neuropathy of the central nervous system (detrusor hyperreflexia), including spinal cord and brain lesions, such as multiple sclerosis and stroke. Overactive bladder symptoms may also result from, for example, male bladder outlet obstruction (usually due to prostatic hypertrophy), interstitial cystitis, local edema and irritation due to focal bladder cancer, radiation cystitis due to radiotherapy to the pelvis, and cystitis.

The compounds of the present invention are used to treat mammals, including man and horse. It is preferred that the mammal is a human.

The compounds according to the invention, in the form of free base or salts with pharmaceutically acceptable acids, or solutions thereof, can be brought into suitable dosage forms, such as compositions for administration through the oral, rectal, transdermal, parenteral, nasal, or pulmonary route in accordance with accepted pharmaceutical procedures. In particular, the compositions may be administered via inhalation or insufflation. Such pharmaceutical compositions according to the invention comprise the compounds according to the invention in association with compatible pharmaceutically acceptable carrier materials, or diluents, as is well known in the art. The carriers may be any inert material, organic or inorganic, suitable for administration, such as: water, gelatin, gum arabicum, lactose, microcrystalline cellulose, starch, sodium starch glycolate, calcium hydrogen phosphate, magnesium stearate, talcum, colloidal silicon dioxide, and the like. Such compositions may also contain other pharmaceutically active agents, and conventional additives such as stabilizers, wetting agents, emulsifiers, flavoring agents, buffers, binders, disintegrants, lubricants, glidants, antiadherents, propellants, and the like.

The novel compounds according to the present invention can be administered in any suitable way. The compounds according to the invention can be made up in solid or liquid form, such as tablets, capsules, powders, syrups, elixirs and the like, aerosols, sterile solutions, suspensions or emulsions, and the like. They are advantageously administered via inhalation or insufflation. When the administration form is inhalation or insufflation, the compounds are preferably in the form of either an aerosol or a powder.

The term "effective amount" refers to a therapeutically effective amount for treating asthma, chronic obstructive pulmonary disease (COPD), allergic rhinitis, rhinorrhea due to the common cold, or urinary disorder. The terms "therapy" and "therapeutically" encompass all kinds of treatments, including prophylaxis. In particular, "therapeutically effective" means that it is effective for anti-cholinergic treatment.

The dosage of the specific compound according to the invention will vary depending on its potency, the mode of administration, the age and weight of the patient and the severity of the condition to be treated.

Doses administered by inhaler, such as a dry powder inhaler (DPI) or a metered-dose inhaler (MDI), are preferably given as one or two puffs, preferably comprising the total daily dose. For a human subject, it is preferred that the dosage is in the range of from 1 microgram (1 µg) to one milligram (1 mg).

Doses administered by nebulizer solution are generally higher than doses administered by inhaler. For a human subject, it is preferred that the total dosage given by nebulizer solution is in the range of from 1 microgram (1 µg) to ten milligrams (10 mg).

Thus, a clinically effective amount of the compounds according to the invention is from about 1 µg to about 10 mg. It is preferred that the effective amount is from about 1 µg to about 1 mg, preferably from about 0.01 mg to about 1 mg.

The compounds of the invention can be administered from one to four times daily. It is preferable to administer the compounds once or twice daily, more preferable once daily.

The dosage form for inhalation can be an aerosol. The minimum amount of an aerosol delivery is about 0.2 ml and the maximum aerosol delivery is about 5 ml. The concentration of the compounds according to the invention may vary as long as the total amount of spray delivered is within the about 0.2 to about 5 ml amount and it delivers an effective amount. It is well known to those skilled in the art that if the concentration is higher, one gives a smaller dose to deliver the same effective amount.

The non-active ingredient or carrier can be just (sterile) water with the pH adjusted to where the active pharmaceutical agent is very soluble. It is preferred that the pH be at or near 7. Alternatively and preferably, the non-active carrier agent should be physiological saline with the pH adjusted appropriately. Aerosols for inhalation of various pharmaceutical agents are well known to those skilled in the art, including many aerosols for treating asthma.

Alternatively, the dosage form for inhalation can be a powder. Powders for inhalation of various pharmaceutical agents are well known to those skilled in the art, including many powders for treating asthma. When the dosage form is a powder, the compounds according to the invention can be administered in pure form or diluted with an inert carrier. When an inert carrier is used, the compounds according to the invention are compounded such that the total amount of powder delivered delivers an "effective amount" of the compounds according to the invention. The actual concentration of the active compound may vary. If the concentration is lower, then more powder must be delivered; if the concentration is higher, less total material must be delivered to provide an effective amount of the active compound according to the invention.

For treatment of rhinitis, in particular rhinitis due to the common cold, the compounds according to the invention can advantageously be administered in combination with steroids, cromoglycates, and decongestants (alpha agonists). Such combination therapies are useful in the treatment of rhinorrhea due to the common cold.

The invention will be further illustrated by the following non-limiting examples and pharmacological tests.

Tolterodine refers to 2-[(1R)-3-(diisopropylamino)-1-phenylpropyl]-4-methylphenol, also known as N,N-diisopropyl-3-(2-hydroxy-5-methylphenyl)-3-phenylpropylamine, a compound of the formula:

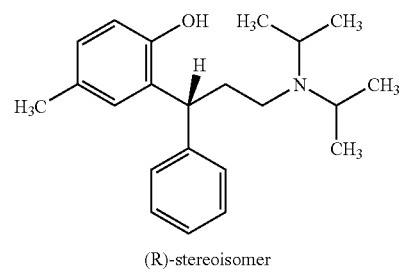

(R)-stereoisomer

Hydroxytolterodine refers to 2-[(1R)-3-(diisopropylamino)-1-phenylpropyl]-4-(hydroxymethyl)phenol, a compound of the formula:

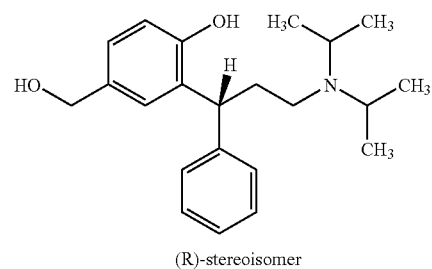

(R)-stereoisomer

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

All temperatures are in degrees Celsius.

Ether refers to diethyl ether.

Physiological saline refers to an 0.9% aqueous sodium chloride solution.

When solvent pairs are used, the ratios of solvents used are volume/volume (v/v).

When the solubility of a solid in a solvent is used the ratio of the solid to the solvent is weight/volume (wt/v).

Example 1

Tolterodine Free Base

Tolterodine tartrate (2.1 g) is mixed with water (45 ml) and toluene (2.5 ml). Sodium carbonate (800 mg) is added to the slurry. Sodium hydroxide (2.0 N, 1.5 ml) is added. The mixture is extracted three times with toluene (3 ml), saving the organic phase. Anhydrous potassium carbonate is added to the organic phase dissolve the tolterodine tartate, giving the title compound in solution.

Example 2

(3R)-3-(2-Hydroxy-5-methylphenyl)-N,N-diisopropyl-N-methyl-3-phenylpropan-1-aminium iodide

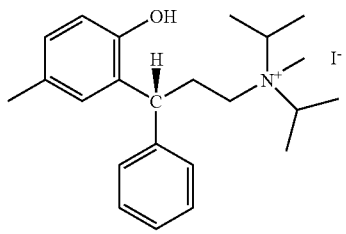

To tolterodine free base (from Example 1, 0.5 M, 2.5 ml) in toluene is added methyl iodide (1 ml). Acetonitrile (5 ml) is added to the mixture and stirred over night at 20-25° C. The solvent is removed by blowing dry nitrogen. Acetone (1 ml) and hexane (2 ml) are added and the mixture is filtered at 20-25° C. to give the title compound. Anal Calcd for $C_{23}H_{34}INO$: C, 59.10; H, 7.33; N, 3.00. Found: C, 59.00; H, 7.44; N, 3.00. The identity of the compound has been further verified and characterised by NMR analysis, mass spectrometry, and melting point determination.

Example 3

(3R)-3-(2-Hydroxy-5-methylphenyl)-N,N-diisopropyl-N-methyl-3-phenylpropan-1-aminium bromide

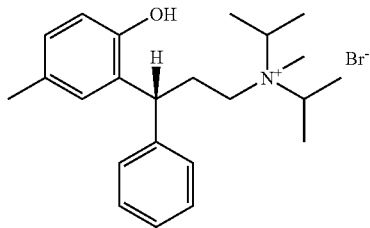

A sealed mixture of methyl bromide (100 g) and 2-[(1R)-3-(diisopropylamino)-1-phenylpropyl]-4-methylphenol (14 g) in acetone (100 ml) is stirred at 20-25° C. for 4 days. The mixture is cooled to −10° C. and the precipitate is filtered off and washed with ether and dried to give the title compound, mp 189-191° C. (dec). Anal Calcd for $C_{23}H_{34}BrNO$: C, 65.71; H, 8.15; Br, 19.00; N, 3.33. Found: C, 65.61; H, 8.34; Br, 19.12; N, 3.32. $[\alpha]_D$ (c=1, MeOH) +25° C. $^1$H NMR $[(CD_3)_2SO]$ δ 1.25, 2.18, 2.48, 2.81, 3.05, 3.89, 4.22, 6.70, 6.83, 7.08, 7.19, 7.33, and 9.3.

Example 4

(3R)-N-Ethyl-3-(2-hydroxy-5-methylphenyl)-N,N-diisopropyl-3-phenylpropan-1-aminium iodide

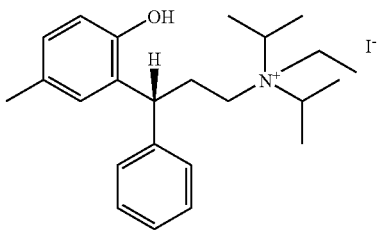

Following the general procedure of Example 2 and making non critical variations, but starting with ethyl iodide, the title compound is obtained.

Example 5

(3R)-3-(2-Hydroxy-5-methylphenyl)-N,N-diisopropyl-3-phenyl-N-propylpropan-1-aminium iodide

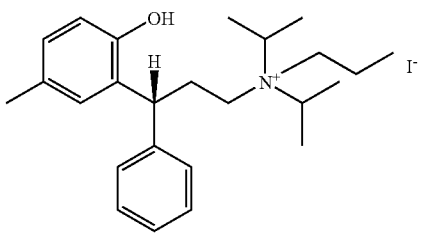

Following the general procedure of Example 2 and making non critical variations, but starting with propyl iodide, the title compound is obtained.

Example 6

(3R)-N-Benzyl-3-(2-hydroxy-5-methylphenyl)-N,N-diisopropyl-3-phenylpropan-1-aminium iodide

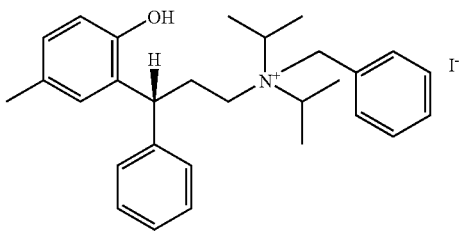

Following the general procedure of Example 2 and making non critical variations, but starting with benzyl iodide, the title compound is obtained.

Example 7

(3R)-N-(tert-Butyl)-3-(2-hydroxy-5-methylphenyl)-N,N-dimethyl-3-phenylpropan-1-aminium bromide

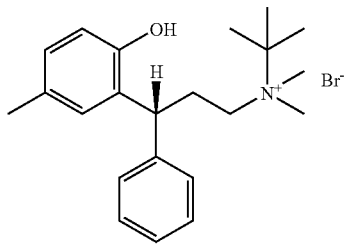

Following the general procedure of Example 2 and making non critical variations, but starting with methyl bromide and 2-{(1R)-3-[tert-butyl(methyl)amino]-1-phenylpropyl}-4-methylphenol, the title compound is obtained.

Example 8

(3R)-3-[2-Hydroxy-5-(hydroxymethyl)phenyl]-N,N-diisopropyl-N-methyl-3-phenylpropan-1-aminium iodide

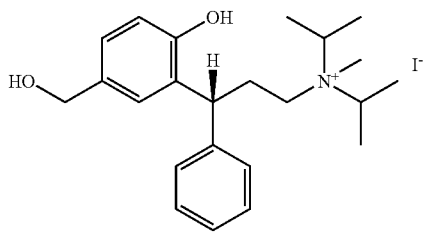

Following the general procedure of Example 2 and making non critical variations, but starting with 2-[(1R)-3-(diisopropylamino)-1-phenylpropyl]-4-(hydroxymethyl)phenol, the title compound is obtained. Anal Calcd for $C_{23}H_{34}INO_2$: C, 57.14: H, 7.09; N, 2.90. Found: C, 56.33; H, 7.33; N, 2.76. HRMS Calcd 356.2589. Found: 356.2588. $^1$H NMR [$(CD_3)_2SO$] δ 1.25, 2.48, 2.81, 3.05, 3.88, 4.26, 4.35, 4.94, 6.75, 6.98, 7.20, 7.33, and 9.5.

Example 9

(3R)-3-(2-Hydroxyphenyl)-N,N-diisopropyl-N-methyl-3-phenylpropan-1-aminium bromide

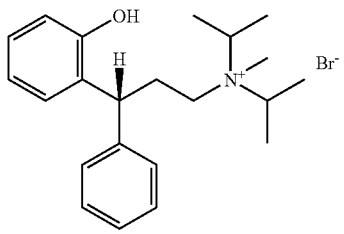

Following the general procedure of Example 3 and making non critical variations but starting with 2-[(1R)-3-(diisopropylamino)-1-phenylpropyl]phenol, the title compound is obtained.

Example 10

(3S)-3-(2-hydroxyphenyl)-N,N-diisopropyl-N-methyl-3-phenylpropan-1-aminium bromide

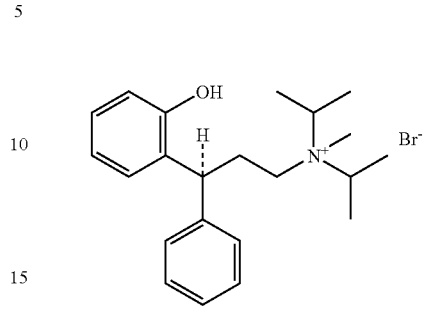

Following the general procedure of Example 3 and making non critical variations, but starting with 2-[(1S)-3-(diisopropylamino)-1-phenylpropyl]phenol, the title compound is obtained.

Example 11

(3R)-3-(5-Chloro-2-hydroxyphenyl)-N,N-diisopropyl-N-methyl-3-phenylpropan-1-aminium bromide

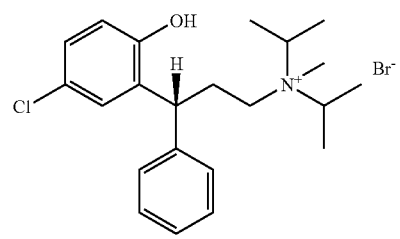

Following the general procedure of Example 3 and making non critical variations, but starting with 4-chloro-2-[(1R)-3-(diisopropylamino)-1-phenylpropyl]phenol, the title compound is obtained.

Example 12

(3R)-3-(5-Bromo-2-hydroxyphenyl)-N,N-diisopropyl-N-methyl-3-phenylpropan-1-aminium bromide

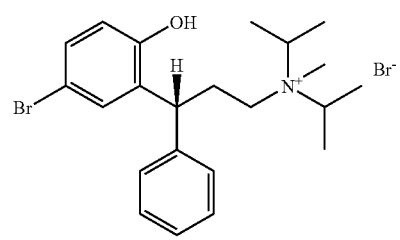

Following the general procedure of Example 3 and making non critical variations, but starting with 4-bromo-2-[(1R)-3-(diisopropylamino)-1-phenylpropyl]phenol, the title compound is obtained.

Example 13

(3R)-3-[2-(Acetyloxy)-5-methylphenyl]-N,N-diisopropyl-N-methyl-3-phenylpropan-1-aminium iodide

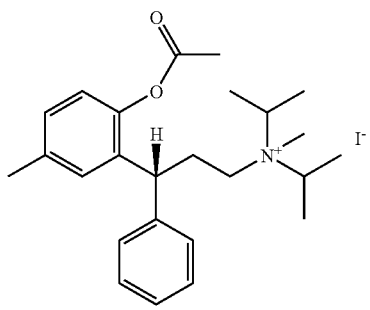

(A) 2-[(1R)-3-(diisopropylamino)-1-phenylpropyl]-4-methylphenyl acetate

A solution of 2-[(1R)-3-(diisopropylamino)-1-phenylpropyl]-4-methylphenol (0.9 g) in acetylchloride (20 ml) is stirred at room temperature for 18 h. The acetyl chloride is evaporated, ether is added, and the precipitate of 2-(1R)-3-(diisopropylamino)-1-phenylpropyl]-4-methylphenyl acetate hydrochloride is filtered off; mp 126-130° C. Anal Calcd for $C_{24}H_{33}NO_2 \cdot HCl$: C, 71.35; H, 8.48; Cl, 8.78; N, 3.47. Found: C, 71.02; H, 8.30; Cl, 8.64; N, 3.43. $[\alpha]_D$ (c=1, MeOH) +11°.

The hydrochloride salt is partitioned between ether and saturated sodium bicarbonate solution. The ether phase is separated and evaporated to obtain the free base of compound (A).

(B) (3R)-3-[2-(acetyloxy)-5-methylphenyl]-N,N-diisopropyl-N-methyl-3-phenylpropan-1-aminium iodide Following the general procedure of Example 2 and making non critical variations, but starting with (A): 2-[(1R)-3-(diisopropylamino)-1-phenylpropyl]-4-methylphenyl acetate, the title compound (B) is obtained.

Example 14

(3R)-3-[2-(Isobutyryloxy)-5-methylphenyl]-N,N-diisopropyl-N-methyl-3-phenylpropan-1-aminium iodide

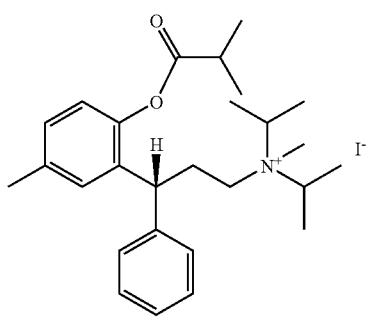

Following the general procedure of Example 2 and making non critical variations, but starting with 2-[(1R)-3-(diisopropylamino)-1-phenylpropyl]-4-methylphenyl 2-methylpropanoate, the title compound is obtained.

Example 15

(3R)-3-(4-Fluorophenyl)-3-(2-hydroxy-5-methylphenyl)-N,N-diisopropyl-N-methylpropan-1-aminium bromide

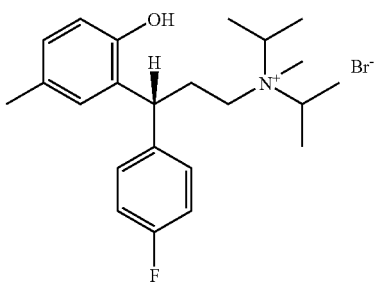

Following the general procedure of Example 3 and making non critical variations, but starting with 2-[(1R)-3-(diisopropylamino)-1-(4-fluorophenyl)propyl]-4-methylphenol, the title compound is obtained.

Example 16

(3R)-3-[2-Hydroxy-5-(trifluoromethyl)phenyl]-N,N-diisopropyl-N-methyl-3-phenylpropan-1-aminium bromide

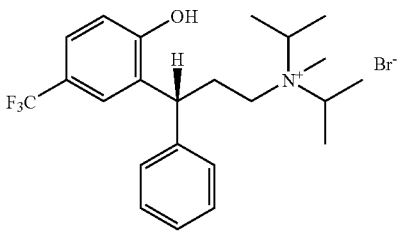

Following the general procedure of Example 3 and making non critical variations, but starting with 2-[(1R)-3-(diisopropylamino)-1-phenylpropyl]-4-(trifluoromethyl)phenol, the title compound is obtained.

Example 17

(3R)-3-[2-(Isobutyryloxy)-5-hydroxymethylphenyl]-N,N-diisopropyl-N-methyl-3-phenylpropan-1-aminium bromide

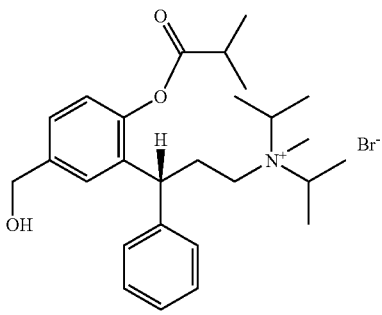

(3R)-3-[2-hydroxy-5-(hydroxymethyl)phenyl]-N,N-diisopropyl-N-methyl-3-phenylpropan-1-aminium bromide is acylated with isobutyryl bromide to give the title compound.

Example 18

(3R)-3-{2-(Acetyloxy)-5-[(acetyloxy)methyl]phenyl}-N,N-diisopropyl-N-methyl-3-phenylpropan-1-aminium bromide

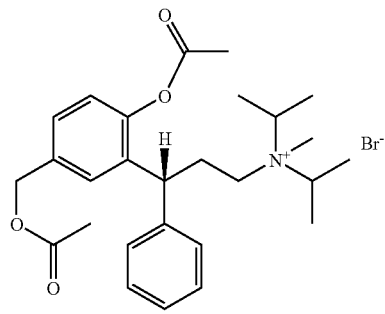

(3R)-3-[2-hydroxy-5-(hydroxymethyl)phenyl]-N,N-diisopropyl-N-methyl-3-phenylpropan-1-aminium bromide is acylated with acetyl bromide, to give the title compound.

Example 19

2-{(1R)-3-[Diisopropyl (methyl)ammonio]-1-phenylpropyl}-4-methylbenzenolate

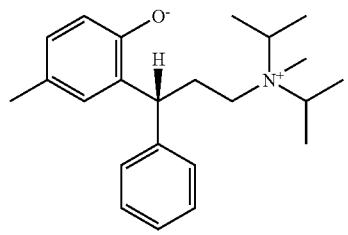

(3R)-3-(2-Hydroxy-5-methylphenyl)-N,N-diisopropyl-N-methyl-3-phenylpropan-1-aminium bromide from Example 2 is passed through an ion exchange column so as to remove the bromide ion and generate the title compound.

Reacting the above compound with an equivalent amount of an acid, such as methanesulfonic acid, hydrochloric acid, acetic acid, or succinic acid, generates other salts of the title compound.

Example 20

(3R)-N,N-Diisopropyl-3-(2-methoxy-5-methylphenyl)-N-methyl-3-phenylpropan-1-aminium iodide

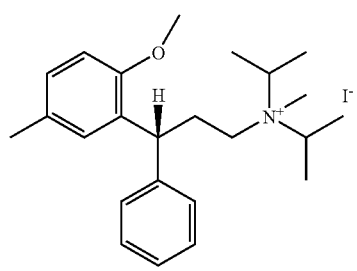

Following the general procedure of Example 2 and making non critical variations, but starting with (3R)-N,N-diisopropyl-3-(2-methoxy-5-methylphenyl)-3-phenylpropan-1-amine, the title compound is obtained; mp 211° C. (dec). Anal Calcd for $C_{24}H_{36}INO$: C, 59.87; H, 7.54; N, 2.91. Found: C, 59.78; H, 7.56; N, 2.99. $[\alpha]_D$ (c=1, MeOH) +13°.

Example 21

(3R)-3-[2-(Butyryloxy)-5-methylphenyl]-N,N-diisopropyl-N-methyl-3-phenylpropan-1-aminium iodide

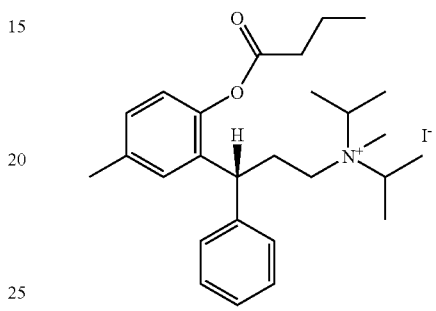

(A) 2-[(1R)-3-(diisopropylamino)-1-phenylpropyl]-4-methylphenyl butyrate

A solution of 2-[(1R)-3-(diisopropylamino)-1-phenylpropyl]-4-methylphenol (1.0 g) in butyryl chloride (5 ml) is heated under reflux for 90 min. Ether is added, and the precipitate of 2-[(1R)-3-(diisopropylamino)-1-phenylpropyl]-4-methylphenyl butyrate hydrochloride is filtered off; mp 116-119° C. Anal Calcd for $C_{26}H_{37}NO_2.HCl$: C, 72.28; H, 8.86; Cl, 8.21; N, 3.24. Found: C, 72.25; H, 8.71; Cl, 8.17; N, 3.25. $[\alpha]_D$ (c=1, MeOH) +20°.

The hydrochloride salt is partitioned between ether and saturated sodium bicarbonate solution. The ether phase is separated and evaporated to obtain the free base of the title compound (A).

(B) (3R)-3-[2-(butyryloxy)-5-methylphenyl]-N,N-diisopropyl-N-methyl-3-phenylpropan-1-aminium iodide Following the general procedure of Example 2 and making non critical variations, but starting with (A) : 2-[(1R)-3-(diisopropylamino)-1-phenylpropyl]-4-methylphenyl butyrate, the title compound is obtained; mp 175° C. (dec). Anal Calcd for $C_{27}H_{40}INO_2$: C, 60.33; H, 7.50; N, 2.61. Found: C, 60.37; H, 7.52; N, 2.58.

Example 22

(3R)-3-(2-Hydroxy-5-methylphenyl)-N,N-diisopropyl-N-methyl-3-phenylpropan-1-aminium iodide

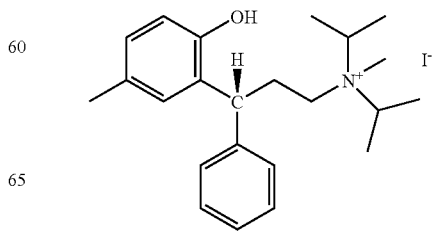

(3R)-3-[2-(butyryloxy)-5-methylphenyl]-N,N-diisopropyl-N-methyl-3-phenylpropan-1-aminium iodide (from Example 22) was hydrolysed with methanol, resulting in the title compound.

Example 23

(3R)-3-(2-Hydroxy-5-methylphenyl)-N,N-diisopropyl-N-methyl-3-phenylpropan-1-aminium chloride

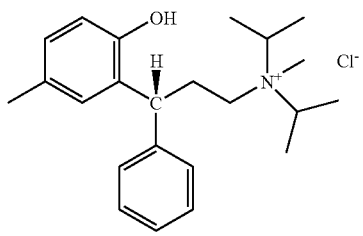

A solution of (3R)-3-(2-hydroxy-5-methylphenyl)-N,N-diisopropyl-N-methyl-3-phenylpropan-1-aminium bromide (4.2 g, 0.01 mol) in water (50 ml) is neutralized by addition of 1 equivalent of 2 N sodium hydroxide solution (5.0 ml). The solvent is evaporated, and the residual oil is chromatographed to separate 2-{(1R)-3-[diisopropyl (methyl) ammonio]-1-phenylpropyl}-4-methylbenzenolate from the sodium bromide. The product is reconstituted in acetone, and a solution of hydrogen chloride in ethyl acetate is added to give a precipitate of the title compound.

Example 24

5-Hydroxy-N-[(3R)-3-(2-hydroxy-5-methylphenyl)-3-phenylpropyl]-N-isopropyl-N-methylpentan-1-aminium iodide

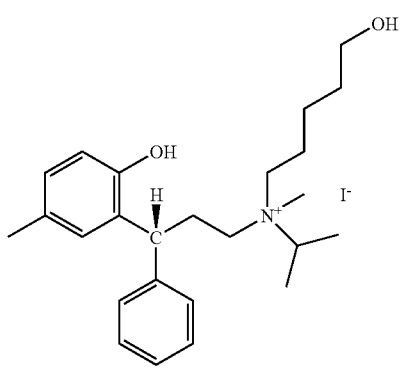

Following the general procedure of Example 2 and making non critical variations, but starting with 2-{(1R)-3-[(5-hydroxypentyl)(isopropyl)amino]-1-phenylpropyl}-4-methylphenol, the title compound is obtained.

Example 25

(3R)-3-(2-Hydroxy-4-methylphenyl)-N,N-diisopropyl-N-methyl-3-phenylpropan-1-aminium iodide

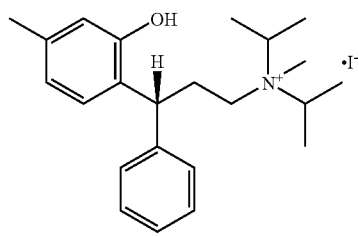

Following the general procedure of Example 2 and making non critical variations, but starting with 2-[(1R)-3-(diisopropylamino)-1-phenylpropyl]-5-methylphenol, the title compound is obtained.

Example 26

3,3-bis(2-Hydroxy-5-methylphenyl)-N,N-diisopropyl-N-methylpropan-1-aminium iodide

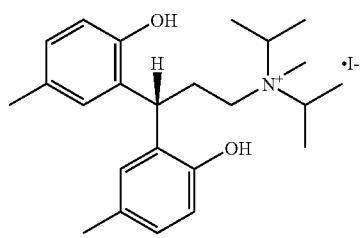

Following the general procedure of Example 2 and making non critical variations, but starting with 2-[3-(diisopropylamino)-1-(2-hydroxy-5-methylphenyl)propyl]-4-methylphenol, the title compound is obtained.

Example 27

(3R)-3-[5-(Aminocarbonyl)-2-hydroxyphenyl]-N,N-diisopropyl-N-methyl-3-phenylpropan-1-aminium iodide

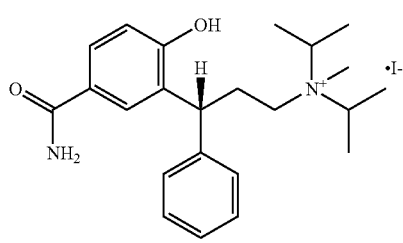

Following the general procedure of Example 2 and making non critical variations, but starting with 3-[(1R)-3-(diisopropylamino)-1-phenylpropyl]-4-hydroxybenzamide, the title compound is obtained.

Example 28

3,3-bis(2-Methoxyphenyl)-N,N-diisopropyl-N-methylpropan-1-aminium iodide

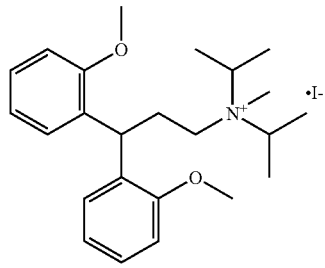

Following the general procedure of Example 2 and making non critical variations, but starting with N,N-diisopropyl-3,3-bis(2-methoxyphenyl)propan-1-amine, the title compound is obtained.

Example 29

Large Scale Production of (3R)-3-(2-hydroxy-5-methylphenyl)-N,N-diisopropyl-N-methyl-3-phenylpropan-1-aminium iodide

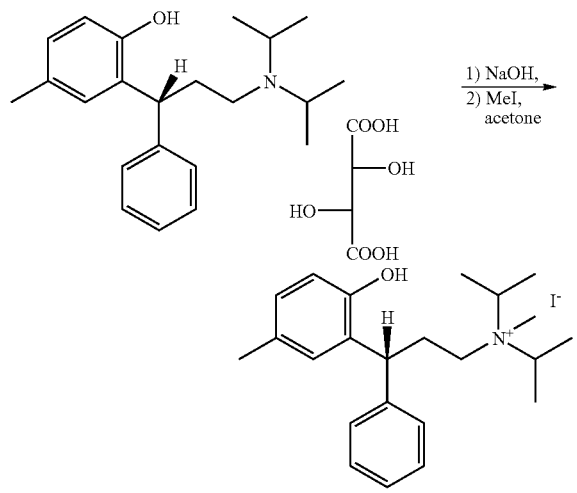

A 5 l erlenmyer flask was charged with 250 g (526 mmol) tolterodine tartrate, water (2000 ml), and methylene chloride (2000 ml). A solution of 84 g of 50% NaOH diluted with 200 ml of water was added, and the mixture was stirred for 1 hour. The pH was kept in the range of 8-9. Both of the two resulting phases are clear and colorless.

The phases were separated, and the aqueous phase was washed with methylene chloride (1000 ml). The combined organic phases were concentrated on the rotovap (60° C. bath). The weight of the residue was determined. The residue was dissolved in acetone (1000 ml), and 263 ml (2.84 mol) methyl iodide was added, all in one portion. The mixture was stirred at room temperature overnight.

The resulting slurry was filtered, washed with acetone (250 ml) and dried in the vacuum oven at 50° C. overnight.

This provided 230 g of the desired product, (3R)-3-(2-hydroxy-5-methylphenyl)-N,N-diisopropyl-N-methyl-3-phenylpropan-1-aminium iodide.

Example 30

Cyclic Amine Intermediates

The following general reductive amination procedure was employed:

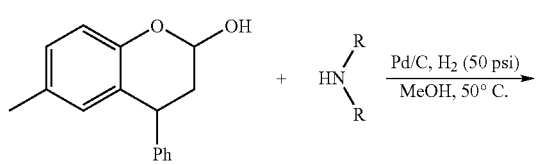

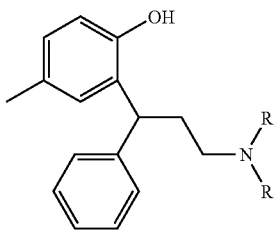

wherein Ph represents a phenyl group, and R represents an alkyl group according to the following Table I.

Briefly, palladium on activated carbon (1.76 g, 5% by weight, Aldrich 20,568-0) was charged to a hydrogenation vessel under nitrogen, followed by a MeOH (20 mL) solution of a racemic lactol (6-methyl-4-phenyl-2-chromanol, see formula above) (4 g, 16.64 mmol) and a secondary amine (42 mmol, 2.5 equiv). The vessel was filled with hydrogen (50 psi), and the reaction mixture was stirred vigorously at 50° C. overnight. The heterogeneous reaction mixture was filtered through celite. The resulting methanolic solution was concentrated under vacuum.

Pure cyclic amines according to the following table I were obtained after trituration with hexanes.

TABLE I

| | Intermediate compounds | |
| --- | --- | --- |
| R | Resulting compound | Yield (%) |
| (CH$_2$)$_4$ | 4-methyl-2-(1-phenyl-3-pyrrolidin-1-ylpropyl) phenol | 71 |

TABLE I-continued

Intermediate compounds

| R | Resulting compound | Yield (%) |
|---|---|---|
| (CH$_2$)$_5$ | 4-methyl-2-(1-phenyl-3-piperidin-1-ylpropyl) phenol | 33 |
| (CH$_2$)$_6$ | 2-(3-azepan-1-yl-1-phenylpropyl)-4-methylphenol | 29 |

Characterization of 4-methyl-2-(1-phenyl-3-pyrrolidin-1-ylpropyl)phenol:

$^1$H NMR (CDCl$_3$): δ 1.90 (m, 4H), 2.09 (s, 4H), 2.25-2.45 (m, 2H), 2.57 (m, 2H), 2.63-2.78 (m, 3H), 4.55 (dd, 1H, J=12 Hz, J=3 Hz), 6.47 (s, 1H), 6.85 (s, 2H), 7.19-7.26 (m, 2H), 7.30 (m, 3H), 11.23 (s, 1H).

$^{13}$C NMR (CDCl$_3$): δ 19.8, 26.0, 33.5, 39.9, 53.5, 54.3, 125.8, 127.3, 128.1, 128.4, 128.7, 131.2145.0, 153.0. ESI mass spectrum: 296 [M+1$^+$], 297 [M+2$^+$].

Characterization of 4-methyl-2-(1-phenyl-3-piperidin-1-ylpropyl)phenol:

$^1$H NMR (CDCl$_3$) : δ 1.52-1.53 (m, 2H), 1.62-1.81 (m, 4H), 1.98 (t, 1H, J=10 Hz), 2.09 (s, 3H), 2.26-2.60 (m, 6H), 4.46 (dd, 1H, J=13 Hz, J=3 Hz), 6.47 (s, 1H), 6.85 (d, 2H, J=0.9 Hz), 7.19-7.24 (m, 2H), 7.30-7.35 (m, 3H), 11.24 (s, 1H).

$^{13}$C NMR (CDCl$_3$): δ 20.9, 24.4, 25.4, 31.3, 38.4, 53.8, 54.7, 61.0, 102.2, 117.9, 126.3, 128.1, 128.4, 128.6, 129.3, 129.4, 131.4, 145.2, 154.3. ESI mass spectrum: 310 [M+1$^+$], 311 [M+2$^+$]

Characterization of 2-(3-azepan-1-yl-1-phenylpropyl)-4-methylphenol:

$^1$H NMR (CDCl$_3$): δ 1.60-1.65 (m, 4H), 1.65-1.85 (m, 4H), 1.95-2.10 (m, 4H), 2.30-2.67 (m, 6H), 2.70-2.80 (m, 2H). $^{13}$C NMR (CDCl$_3$): δ 19.6, 26.6, 26.7, 32.0, 40.7, 55.1, 55.7, 115.9, 125.8, 127.3, 128.0, 128.1 128.5, 128.7, 131.4, 145.1, 153.0, 145.2, 152.8. ESI mass spectrum: 324 [M+1$^+$], 325 [M+2$^+$].

Example 31

1-[3-(2-Hydroxy-5-methylphenyl)-3-phenylpropyl]-1-methylpyrrolidinium iodide

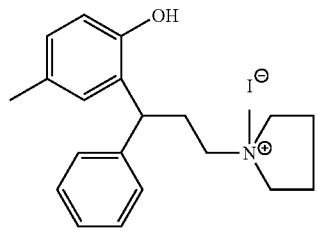

Methyl iodide (10 equivalents) was added to a solution of the free base 4-methyl-2-(1-phenyl-3-pyrrolidin-1-ylpropyl) phenol of Example 30 (0.3 g, 1.02 mmol) in acetone (4 mL). The reaction mixture is stirred overnight at room temperature. The solution is concentrated to initiate the precipitation of the resulting quaternary ammonium salt. The white precipitate is filtered, washed with diethyl ether and dried under vacuum to give a quaternized salt.

White crystals were obtained with a yield of 79%. The resulting compound was characterized:

$^1$H NMR (MeOH-d$_4$): δ 2.05-2.18 (m, 4H), 2.20 (s, 3H), 2.46-2.62 (m, 2H), 3.08 (s, 3H), 3.14-3.40 (m, 2H), 3.40-3.62 (m, 4H), 4.40 (t, 1H, J=7.3 Hz), 6.68 (d, 1H, J=8Hz), 6.85 (d, 1H, J=8 Hz), 6.98 (d, 1H, J=1.5 Hz), 7.16-7.23 (m, 1H), 7.30 (t, 2H, J=7 Hz), 7.37-7.42 (m, 2H). $^{13}$C NMR (MeOH-d$_4$): δ 19.3, 21.5, 28.2, 41.5, 46.8, 63.6, 64.5, 115.2, 126.5, 127.9, 128.0, 128.4, 128.5, 128.9, 129.2, 143.4, 152.5. Elemental analysis, C$_{21}$H$_{28}$INO: Found(%): C 57.64, H 6.43, I 28.77, N 3.23, O 3.88; Theory(%): % C 57.67, H 6.45, I 29.02, N 3.20, O 3.66. ESI mass spectrum for C$_{21}$H$_{28}$NO+: 310.2.

Example 32

1-Ethyl-1-[3-(2-hydroxy-5-methylphenyl)-3-phenylpropyl]pyrrolidinium iodide

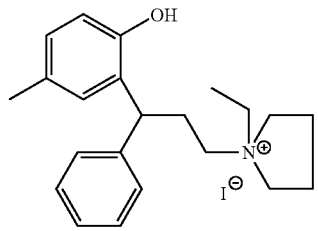

Ethyl iodide (10 equivalents) was added to a solution of the free base 4-methyl-2-(1-phenyl-3-pyrrolidin-1-ylpropyl) phenol of Example 30 (0.3 g, 1.02 mmol) in acetone (4 mL). The reaction mixture is stirred overnight at room temperature. The solution is concentrated to initiate the precipitation of the resulting quaternary ammonium salt. The white precipitate is filtered, washed with diethyl ether and dried under vacuum to give a quaternized salt.

White crystals were obtained with a yield of 81%. The resulting compound was characterized:

$^1$H NMR (MeOH-d$_4$): δ 1.24 (t, 3H, J=7 Hz), 2.0-2.18 (m, 4H), 2.20 (s, 3H), 2.40-2.63 (m, 2H), 3.08-3.25 (m, 2H), 3.35-3.60 (m, 6H), 4.38 (t, 1H, J=7.5 Hz), 6.70 (d, 1H, J=8 Hz), 6.85 (d, 1H, J=8 Hz), 7.0 (d, 1H, J=1.4 Hz), 7.16-7.23 (m, 1H), 7.30 (t, 2H, J=7 Hz), 7.37-7.42 (m, 2H).

$^{13}$C NMR (MeOH-d$_4$): δ 8.0, 19.5, 21.5, 28.0, 41.9, 54.7, 58.0, 64.5, 117.8, 126.4, 127.9, 128.1, 128.4, 128.7, 128.9, 129.2, 143.6, 152.8. Elemental analysis, C$_{22}$H$_{30}$INO: Found(%) : C 58.17, H 6.65, I 27.79, N 3.10, O 3.62; Theory(%): C 58.54, H 6.70, I 28.11, N 3.10, O 3.54. ESI mass spectrum for C$_{22}$H$_{30}$NO$^+$: 324.2.

Example 33

1-[3-(2-Hydroxy-5-methylphenyl)-3-phenylpropyl]-1-methylpiperidinium iodide

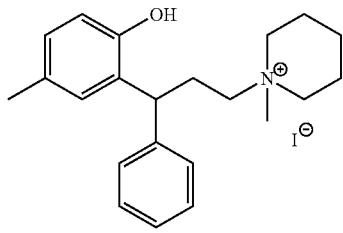

Methyl iodide (3.42 g, 1.5 mL, 0.024 mol) was added to a solution of the free base 4-methyl-2-(1-phenyl-3-piperidin-1-ylpropyl)phenol of Example 30 (0.3 g, 0.97 mmol) in a mixture of acetonitrile (6 mL) and acetone (2 mL). The reaction mixture was stirred overnight at room temperature. The solution was concentrated to initiate precipitation of the resulting quaternary ammonium salt. The white precipitate was filtered out, washed with chloroform and diethyl ether and dried under vacuum to give 0.397 g (90%) of the title compound. Characterization of the obtained compound:

$^1$H NMR (MeOH-d$_4$) : δ 1.57-1.84 (m, 6H), 2.19 (s, 3H), 2.46-2.64 (m, 2H), 3.06 (s, 3H), 3.14-3.4 (m, 6H), 4.39 (t, 1H, J=7.3 Hz), 6.68 (d, 1H, J=8 Hz), 6.85 (dd, 1H, J=8 Hz, J=1.5 Hz), 7.0 (d, 1H, J=1.5 Hz), 7.18 (t, 1H, J=8 Hz), 7.29 (t, 1H, J=7.4 Hz), 7.37-7.4 (m, 5H).

$^{13}$C NMR MeOH-d$_4$): δ 19.5, 19.7, 19.8, 20.7, 26.7, 41.5, 60.9, 61.2, 114.0, 115.1, 126.3, 127.9, 128.0, 128.4, 128.5, 128.9, 129.2, 143.4, 152.4.

Example 34
1-[3-(2-Hydroxy-5-methylphenyl)-3-phenylpropyl]-1-methylazepanium iodide

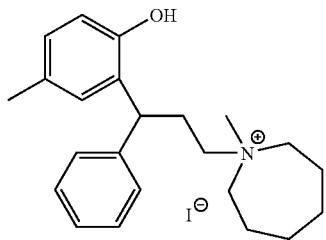

Methyl iodide (10 equivalents) was added to a solution of the free base 2-(3-azepan-1-yl-1-phenylpropyl)-4-methylphenol of Example 30 (0.3 g, 1.02 mmol) in CH$_2$Cl$_2$ (2 mL). The reaction mixture was stirred overnight at room temperature. The solution was concentrated to initiate precipitation of the resulting quaternary ammonium salt. The white precipitate was filtered out, washed with diethyl ether and dried under vacuum to give a quaternized salt.

White crystals were obtained with a yield of 77%. The resulting compound was characterized:

$^1$H NMR (MeOH-d$_4$): δ 1.6-2.0 (m, 8H), 2.01 (s, 3H), 2.40-2.70 (m, 2H),), 3.10 (s, 3H), 3.15-3.60 (m, 6H), 4.38 (t, 1H, J=7 Hz), 6.68 (d, 1H, J=8Hz), 6.88 (d, 1H, J=8 Hz), 7.05 (s, 1H), 7.18-7.24 (m, 1H), 7.25-7.40 (m, 5H).

$^{13}$C NMR (MeOH-d$_4$): δ 20.8, 22.4, 27.5, 41.6, 50.2, 59.2, 63.8, 64.5, 64.8, 117.5, 126.3, 127.95, 128.03, 128.4, 128.6, 128.9, 129.2, 143.4, 152.5. ESI mass spectrum for C$_{23}$H$_{32}$NO$^+$: 338.2.

The usefulness of the compounds according to the invention is further illustrated by the following examples.

Example I

Binding Data

Muscarinic receptor subtype M$_1$-M$_5$ binding assays were carried out. Briefly, $^3$H-methylscopolamine was allowed to bind to membranes from various recombinant mammalian cell lines, each with an over-expression of a particular receptor subtype. An equilibrium radioligand displacement assay was performed using the title compound of example 2, (3R)-3-(2-Hydroxy-5-methylphenyl)-N,N-diisopropyl-N-methyl-3-phenylpropan-1-aminium iodide (a quaternary ammonium compound according to the invention), and for comparison the following anticholinerigic agents: tolterodine, hydroxytolterodine, ipratropium, and atropine. The resulting K$_i$ values, displayed in Table II, are averages of duplicate samples at each dose in an 11-point dose-response curve, using half-log intervals.

TABLE II

| | K$_i$ values (nM) | | | | |
| --- | --- | --- | --- | --- | --- |
| | Displacing compound | | | | |
| Receptor subtype | (3R)-3-(2-Hydroxy-5-methylphenyl)-N,N-diisopropyl-N-methyl-3-phenylpropan-1-aminium iodide | Tolterodine | Hydroxytolterodine | Ipratropium | Atropine |
| M$_1$ | 0.33 | 0.87 | 1.5 | 0.46 | 0.25 |
| M$_2$ | 0.45 | 0.73 | 0.33 | 0.17 | 0.43 |
| M$_3$ | 0.20 | 2.1 | 1.4 | 0.38 | 0.87 |

TABLE II-continued

| | $K_i$ values (nM) | | | | |
|---|---|---|---|---|---|
| | Displacing compound | | | | |
| Receptor subtype | (3R)-3-(2-Hydroxy-5-methylphenyl)-N,N-diisopropyl-N-methyl-3-phenylpropan-1-aminium iodide | Tolterodine | Hydroxytolterodine | Ipratropium | Atropine |
| $M_4$ | 0.39 | 1.5 | 1.4 | 0.42 | 0.48 |
| $M_5$ | 0.25 | 0.55 | 0.48 | 0.54 | 0.47 |

Thus, the title compound of example 2, (3R)-3-(2-hydroxy-5-methylphenyl)-N,N-diisopropyl-N-methyl-3-phenylpropan-1-aminium iodide, according to the invention has high affinity and little or no selectivity for any of the muscarinic receptor $M_1$-$M_5$ subtypes. Obtained $K_i$ values for (3R)-3-(2-Hydroxy-5-methylphenyl)-N,N-diisopropyl-N-methyl-3-phenylpropan-1-aminium iodide are in the same range as $K_i$ values for tolterodine, hydroxytolterodine, ipratropium, and atropine.

Example II

Bronchodilatory Effect of Inhaled Quaternary Ammonium Salts in Balb/c Mice

Female BALB/c mice, weight range 19-22 g, were obtained from Charles River Laboratories (Kingston, N.C.).

They received food and water ad libitum. All procedures in these studies were in compliance with the Animal Welfare Act Regulation, 9CFR Parts 1 and 2, Publication (NIH) 85-23, 1985.

Compounds for aerosol administration were prepared in sterile Dulbecco's Phosphate Buffered Saline.

Mice were placed in a carousel-style, nose only, exposure chamber and allowed to inhale aerosols for five minutes, using an ICN SPAG-2 nebulizer. This nebulizer generates a mean aerosol particle size of 1.3 microns at a rate of approximately 0.25 ml/minute.

Ten minutes, 4 hours, 8 hours, 24 hours, 36 hours or 48 hours later, the mice were moved to whole body plethysmograph chambers. Bronchoconstriction was induced in mice by administration of an 80 mg/ml methacholine (MC) aerosol into the plethysmograph chambers for 5 minutes. The mice were allowed to inhale an aerosol containing 80 mg/ml methacholine following inhalation treatment with vehicle, or 80 mg/ml methacholine following inhalation treatment with 0.072, 0.144, or 1.44 mg/ml of the title compound of example 2, i.e. (3R)-3-(2-hydroxy-5-methylphenyl)-N,N-diisopropyl-N-methyl-3-phenylpropan-1-aminium iodide, or 80 mg/ml methacholine following inhalation treatment with 1.24 mg/ml ipratropium bromide. The average enhanced pause (lung resistance) was determined. In order to determine the baseline, saline aerosol (without methacholine) was also separately administered to the mice.

Figure 2:
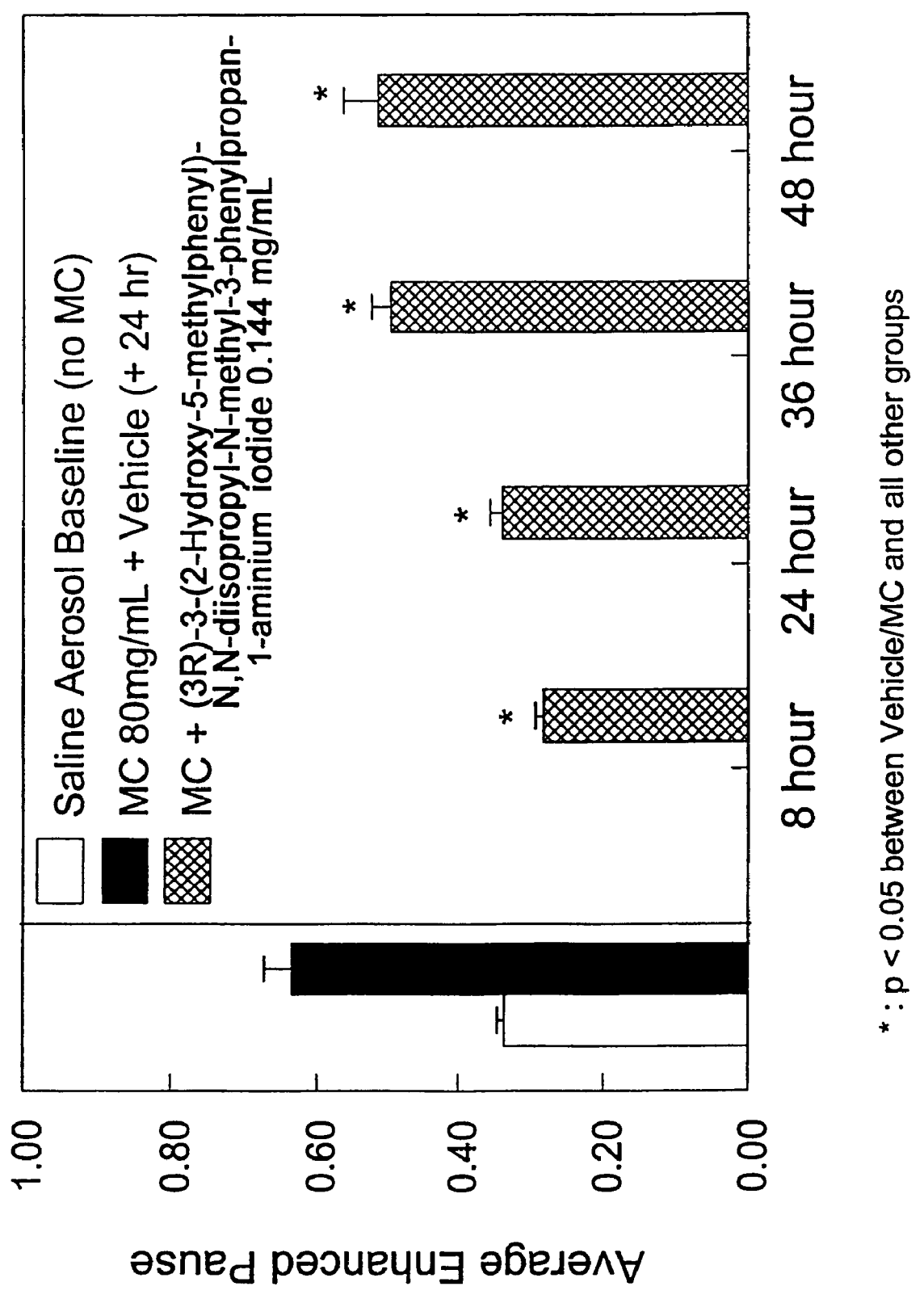
Figure 3:
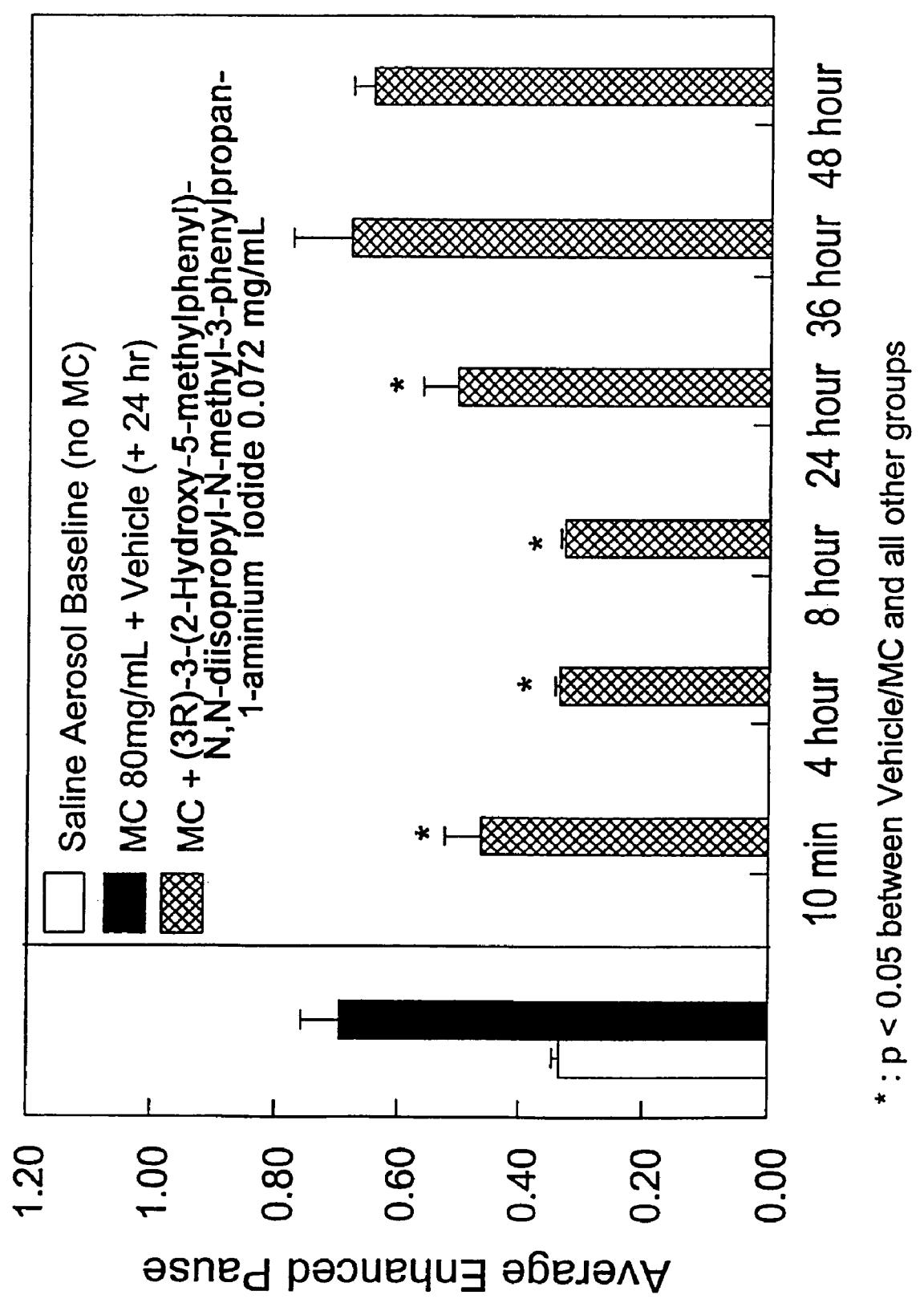

The results are shown in FIG. 1 (1.44 mg/ml of the title compound of example 2 and 1.24 mg/ml ipratropium bromide), FIG. 2 (0.144 mg/ml of the title compound of example 2), and FIG. 3 (0.072 mg/ml of the title compound of example 2).

Increasing doses of the title compound of example 2 produce increasing durations of action. In FIG. 1, inhalation of aerosols generated from a solution containing 1.44 mg/ml of the title compound of example 2 produced a complete block of methacholine-induced bronchoconstriction through 36 hours following administration. Ipratopium bromide (1.24 mg/ml) did not display an equally sustained action. Inhalation of aerosols generated from solutions containing 0.144 mg/ml (FIG. 2) or 0.072 mg/ml (FIG. 3), respectively, of the title compound of example 2 prevented methacholine-induced bronchoconstriction through 24 or 8 hours, respectively, following administration.

Example III

Bronchodilatory Effect of Inhaled Quaternary Ammonium Salts in Balb/c Mice

Female BALB/c mice were obtained and fed as in example II. Compounds were prepared and administered to the mice (aerosol) as in example II.

Ten minutes, 30 minutes, 1 hour, 2 hours or 4 hours later, the mice were placed in plethysmograph chambers, and bronchoconstriction was induced in the mice by administration of an 80 mg/ml methacholine aerosol. The mice were allowed to inhale an aerosol containing 80 mg/ml methacholine following inhalation with vehicle, or 80 mg/ml methacholine following inhalation treatment with 1.46 mg/ml tolterodine, or 80 mg/ml methacholine following inhalation treatment with 1.44 mg/ml of the title compound of example 2, i.e. (3R)-3-(2-hydroxy-5-methylphenyl)-N,N-diisopropyl-N-methyl-3-phenylpropan-1-aminium iodide.

Figure 4:
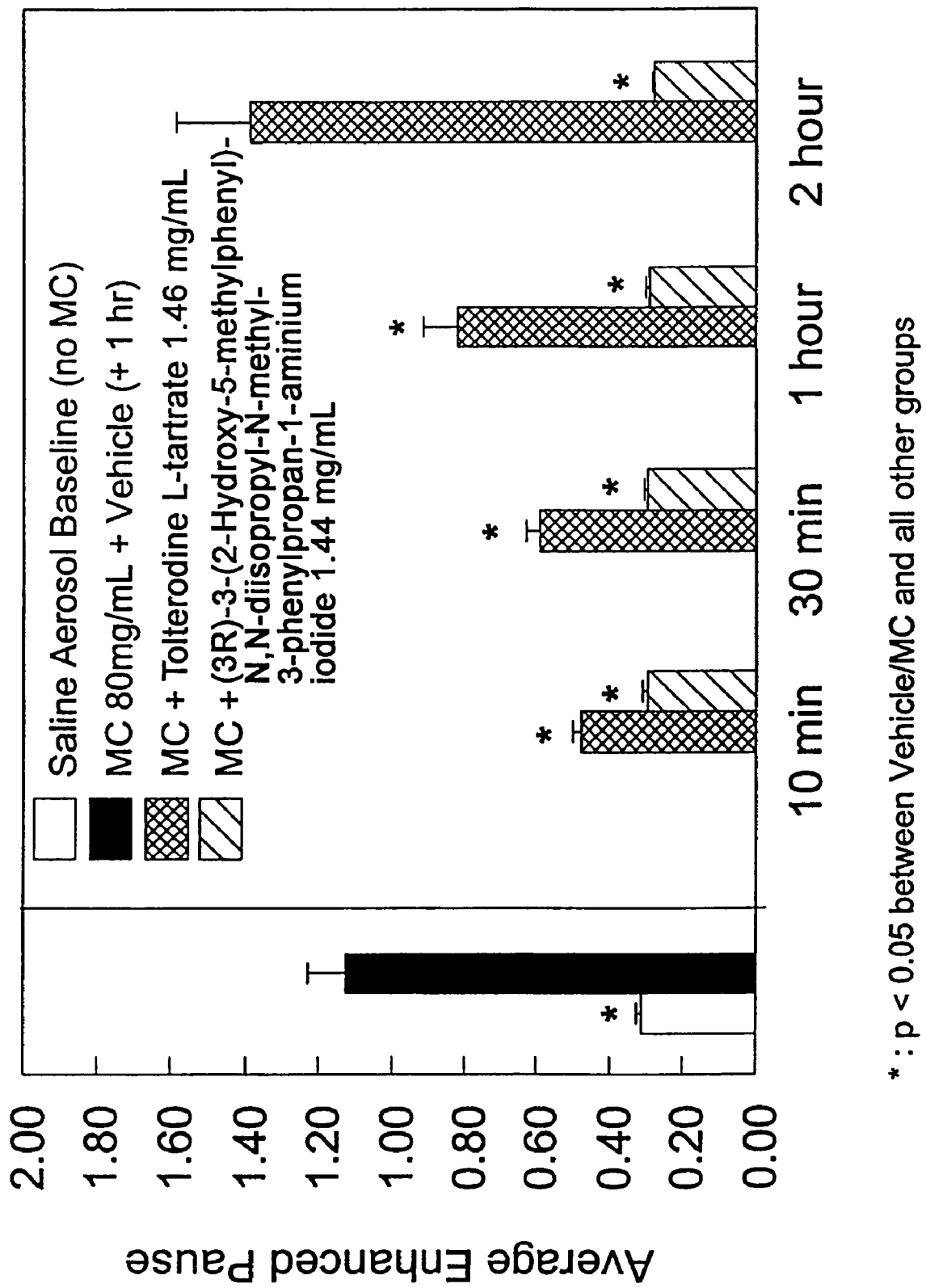
FIG. 4 is a diagram showing the effects of inhalation of tolterodine and a compound according to the invention, respectively, on the average enhanced pause (lung resistance) as a function of time in Balb/c mice.

The results are shown in FIG. 4. It is obvious from FIG. 4 that the title compound of example 2 has a pronounced effect on lung resistance. In addition, the bronchodilatory effects of the title compound of example 2 exhibit a prolonged duration.

Example IV

Bronchodilatory Effect of Inhaled Quaternary Ammonium Salts in Balb/c Mice

Female BALB/c mice were obtained and fed as in example II. Compounds were prepared and administered to the mice (aerosol) as in example II.

Ten minutes, 2 hours, 4 hours, 8 hours or 24 hours later, the mice were placed in plethysmograph chambers, and bronchoconstriction was induced in the mice by administration of an 80 mg/ml methacholine aerosol. The mice were allowed to inhale an aerosol containing 80 mg/ml methacholine following inhalation with vehicle, or 80 mg/ml methacholine following inhalation with 1.44 mg/ml of the title compound of example 2, i.e. (3R)-3-(2-hydroxy-5-methylphenyl)-N,N-diisopropyl-N-methyl-3-phenylpropan-1-aminium iodide, or 80 mg/ml methacholine following inhalation with 1.24 mg/ml ipratropium bromide.

Figure 5:
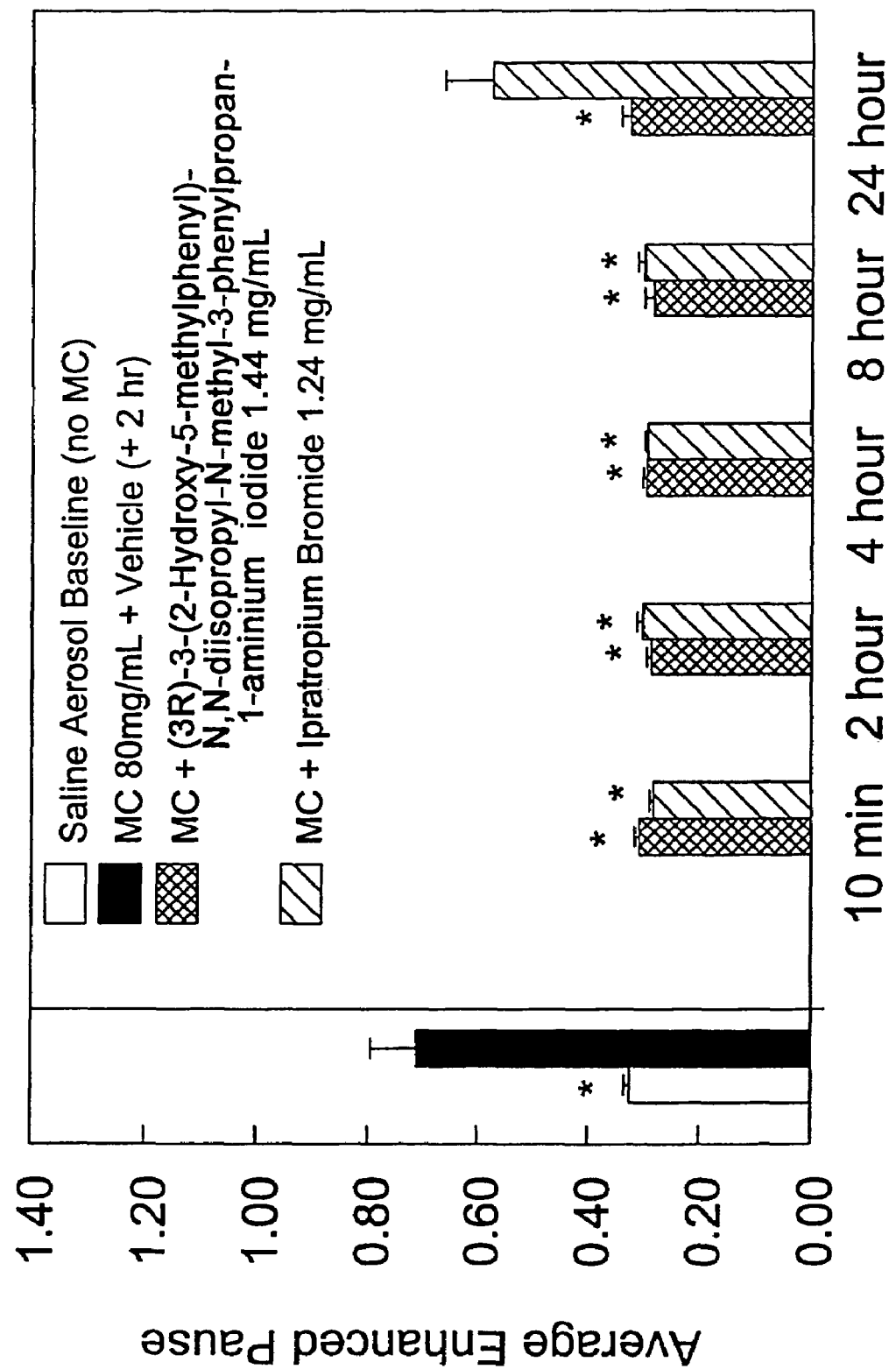
FIG. 5 is a diagram showing the effects of inhalation of a compound according to the invention and ipratropium bromide, respectively, on the average enhanced pause (lung resistance) as a function of time in Balb/c mice.

The results are shown in FIG. 5. It can be concluded that the bronchodilatory effects of the title compound of example 2 have a longer duration when compared to ipratropium bromide.

Example V

Pharmacokinetics of Inhaled Quaternary Ammonium Salts in Balb/c Mice

Blood samples were taken from the mice in example II via cardiac puncture under isoflurane anesthesia at 2.5 minutes, 10 minutes, 30 minutes, 2 hours, 4 hours, 8 hours, or 12 hours after aerosol drug treatment.

The samples were collected in tubes containing EDTA and centrifuged at 12000×g for four minutes. Plasma was removed and stored at −70° C. until assay.

Plasma samples were extracted via a liquid/liquid extraction technique. Plasma levels of the title compound of example 2 were determined by ESI-LC/MS/MS using a PE SCIEX API 4000 mass spectrometer in positive ion mode. Chromatographically, the analyte and the internal standard were resolved on a Phenomenex Phenyl-Hexyl column using an isocratic elution. The limit of quantitation was 24 pg/ml.

Figure 6:
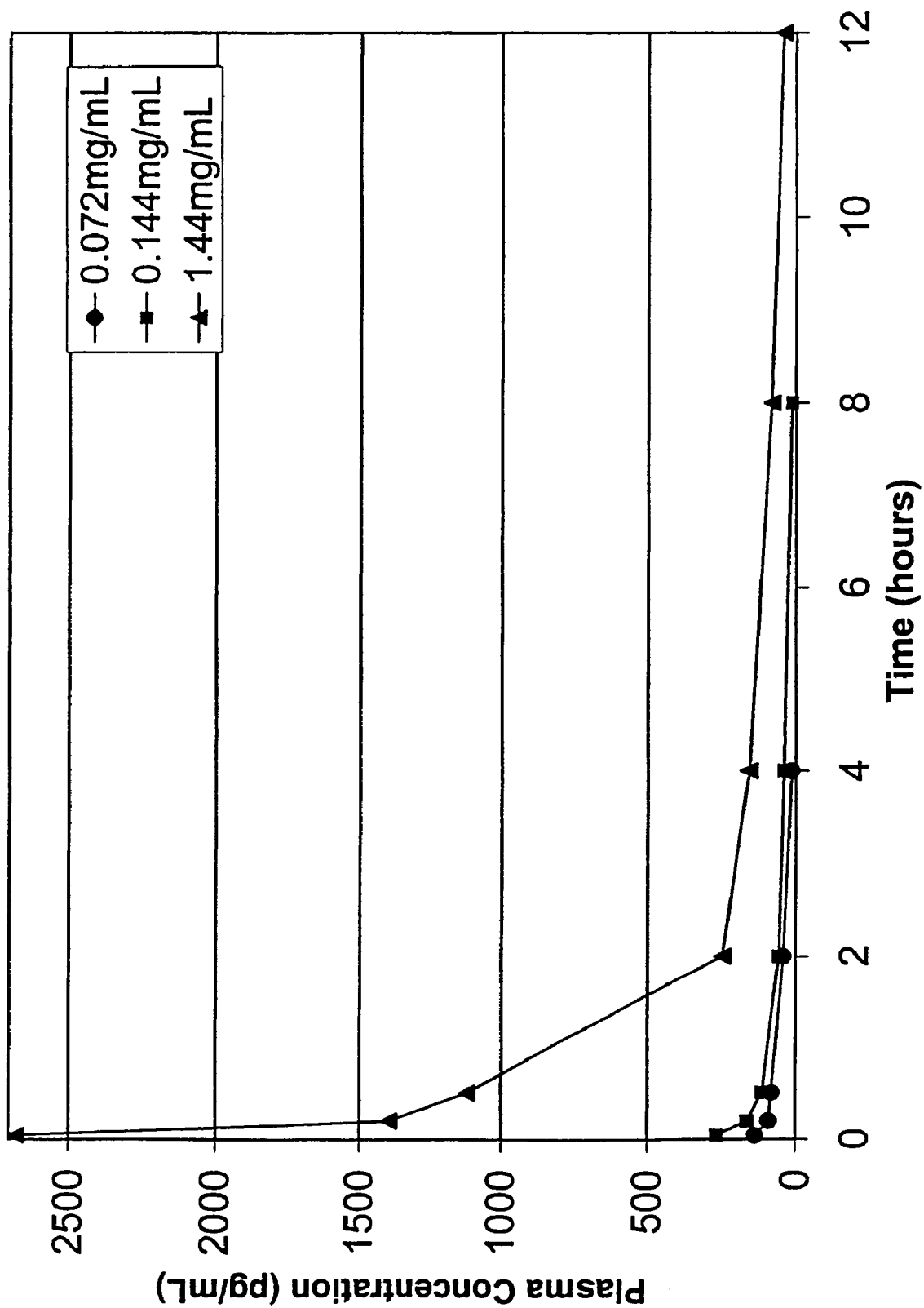
FIG. 6 is a diagram showing the plasma concentration (pg/ml) of a compound according to the invention with time (hours) following aerosol administration of various amounts in Balb/c mice.

Plasma concentrations of the title compound of example 2 following aerosol exposure (inhalation) are summarized in table III and FIG. 6.

TABLE III

Plasma concentration

| Time | Plasma concentration ± std dev (pg/ml) following inhalation of various conc. | | |
|---|---|---|---|
| | 0.072 mg/ml | 0.144 mg/ml | 1.44 mg/ml |
| 2.5 min | 136 ± 38 | 264 ± 21 | 2675 ± 389 |
| 10 min | 90 ± 1 | 162 ± 11 | 1395 ± 163 |
| 30 min | 81 ± 8 | 112 ± 10 | 1120 ± 42 |
| 2 h | 41 ± 6 | 55 ± 7 | 245 ± 3 |
| 4 h | 14 ± 1 | 40 ± 3 | 157 ± 2 |
| 8 h | — | 12 ± 1 | 80 ± 2 |
| 12 h | — | — | 42 ± 2 |

The doses given to the lungs were proportional to the concentrations appearing in the plasma. Importantly, the systemic (plasma) exposure was very low, which indicates that the title compound of example 2 resides for a prolonged time in the lung. This correlates well with its long duration of action.

Example VI (Comparative) Pharmacokinetics of Inhaled Tolterodine in Balb/c Mice

Female BALB/c mice were obtained and fed as in example II. Tolterodine L-tartrate for aerosol administration was prepared in sterile phosphate buffer solution at concentrations of 0.1, 0.5, and 1.0 mg/ml, and administered to the mice (aerosol) as in example II.

Blood samples were collected at 2.5 minutes, 15 minutes, 30 minutes, 1 hour or 2 hours after aerosol drug treatment. Blood samples were prepared as in example VI. Samples were analyzed using a PE SCIEX API 3000 mass spectrometer. Chromatographically, the analyte and the internal standard were resolved on a Zorbax ACE Phenyl column using a gradient elution. The limit of quantitation was 100 pg/mL.

Figure 7:
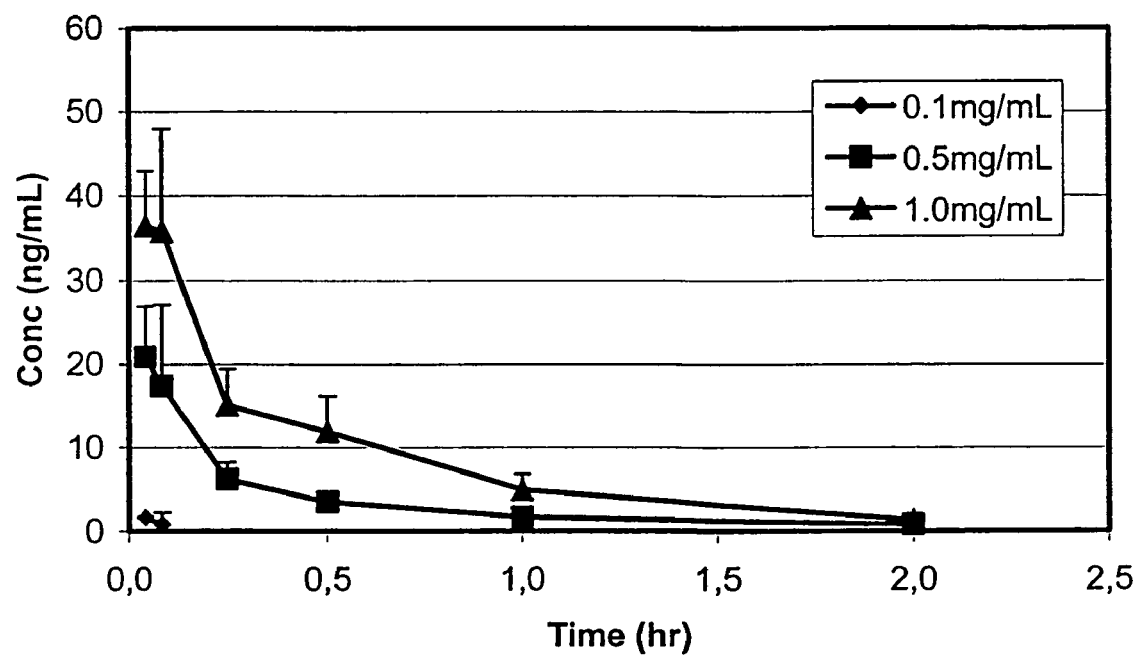
FIG. 7 is a diagram showing the plasma concentration (ng/ml) of tolterodine with time (hours) following aerosol administration of various amounts in mice.

FIG. 7 shows plasma concentrations of tolterodine following inhalation of nebulized solutions at 0.1, 0.5, or 1.0 mg/ml. Plasma levels for the 0.1 mg/ml concentration were at or below detection limits. Clearly, tolterodine is rapidly absorbed into the circulation. The plasma level of tolterodine is approximately one order of magnitude higher than the corresponding level of the the title compound of example 2 (example V, FIG. 6).

This demonstrates that while tolterodine is rapidly spread systemically, the compounds according to the invention have an increased duration of action, with implications locally (i.e. for treating asthma, chronic obstructive pulmonary disease (COPD), allergic rhinitis, or rhinorrhea due to the common cold).

Example VII

Binding Data

Muscarinic receptor subtype $M_1$-$M_5$ binding assays were performed. $K_i$ values were determined for the title compounds of examples 3, 8, and 31-34 (all quaternary ammonium compounds according to the invention). The resulting $K_i$ values are displayed in Table IV.

TABLE IV

| Receptor subtype | $K_i$ values (nM) Title compound of Example no | | | | | |
|---|---|---|---|---|---|---|
| | 3 | 8 | 31 | 32 | 33 | 34 |
| $M_1$ | 0.3 | 0.86 | 1.2 | 1.1 | 1.1 | 1 |
| $M_2$ | 0.52 | 1.08 | 2.2 | 1.7 | 1.7 | 1 |
| $M_3$ | 0.43 | 0.92 | 3.3 | 3.1 | 3.2 | 4.7 |
| $M_4$ | 0.72 | 1.07 | 4.2 | 3.8 | 3.6 | 2.9 |
| $M_5$ | 0.26 | 0.68 | 1.6 | 1.2 | 0.9 | 1.8 |

Thus, the title compounds of Example nos 3, 8, and 31-34 according to the invention have high affinity and little or no selectivity for any of the muscarinic receptor $M_1$-$M_5$ subtypes.

Example VIII

Bronchodilatory Effect of Inhaled Quaternary Ammonium Salts in Balb/c Mice

Bronchoconstriction was induced in BALB/c mice by administration of methacholine. The title compounds of Examples 3, 8, and 31-34 (all quaternary ammonium compounds according to the invention) were administered to the mice via inhalation of 1 mg/mL (free base equivalents (FBE)) of each compound. The resulting inhibition of methacholine-induced bronchoconstriction was determined at 10 min as well as 24 h and 48 h, or 36 h, after dosing. The results are displayed in the following Table V.

TABLE V

| Title compound of example no | % inhibition of bronchoconstriction after | | | |
|---|---|---|---|---|
| (1 mg/mL FBE) | 10 min | 24 h | 36 h | 48 h |
| 3 | 100 | | 93 | |
| 8 | 82 | 60 | | 15 |
| 31 | 100 | | 0 | |
| 32 | 100 | | 17 | |
| 33 | 100 | | 0 | |
| 34 | 100 | | 0 | |

Example A

A 65 year old female with a history of chronic COPD with $FEV_1$ of 1.5 liters is treated with (3R)-3-(2-hydroxy-5-methylphenyl)-N,N-diisopropyl-N-methyl-3-phenylpropan-1-aminium iodide in an aerosol formulation, 1 mg every 12 hr continuously for dyspnea. After two weeks of therapy, dyspnea tolerance is improved.

Example B

A 50 year old male with a history of chronic COPD with $FEV_1/FVC$ of 60% is treated with (3R)-3-(2-hydroxy-5-methylphenyl)-N,N-diisopropyl-N-methyl-3-phenylpropan-1-aminium bromide in an aerosol formulation, 2 mg every 8 hr continuously for dyspnea. After a week of treatment, the $FEV_1/FVC$ ratio improves to about 65%.

Example C

A 25 year old female with a history of asthma with a morning peak flow of less than 2 l/sec is treated with (3R)-3-(2-hydroxy-5-methylphenyl)-N,N-diisopropyl-N-methyl-3-phenylpropan-1-aminium iodide powder, 0.1 mg every 8 hr continuously. Treatment improves the peak flow to 4-5 l/sec.

Example D

A 35 year old male with a history of severe asthma with a morning peak flow of 5 l/sec is treated with (3R)-3-(2-hydroxy-5-methylphenyl)-N,N-diisopropyl-N-methyl-3-phenylpropan-1-aminium bromide powder, 6 mg once a day continuously. After a week of treatment, the peak flow improves to 9 l/sec.

Example E

A 45 year old female with a history of severe asthma with a morning peak flow of less than 3 l/sec is treated with (3R)-3-(2-hydroxy-5-methylphenyl)-N,N-diisopropyl-N-methyl-3-phenylpropan-1-aminium iodide in an aerosol formulation, 2 mg three times daily continuously. After a week of treatment the peak flow improves to 6 l/sec.

The invention claimed is:
1. 2-[(1R)-3-(diisopropylamino)-1-phenylpropyl]-4-(trifluoromethyl) phenol.
2. A process for preparing the compound (3R)-3-[2-hydroxy-5-(trifluoromethyl)phenyl]-N,N-diisopropyl-N-methyl-3-phenylpropan-1-aminium bromide, comprising reacting methyl bromide and 2-[(1R)-3-(diisopropylamino)-1-phenylpropyl]-4-(trifluoromethyl) phenol.

* * * * *